United States Patent
Bernardes et al.

(10) Patent No.: US 12,370,185 B2
(45) Date of Patent: Jul. 29, 2025

(54) TRPV2 ANTAGONISTS

(71) Applicant: Instituto de Medicina Molecular João Lobo Antunes, Lisbon (PT)

(72) Inventors: Gonçalo Bernardes, Lisbon (PT); Tiago Rodrigues, Lisbon (PT); João Conde, Lisbon (PT); Charlotte Baker, Lisbon (PT)

(73) Assignee: FUNDAÃO GIMM—GULBENKIAN INSTITUTE FOR MOLECULAR MEDICINE, Lisbon (PT)

( * ) Notice: Subject to any disclaimer, the term of this patent is extended or adjusted under 35 U.S.C. 154(b) by 775 days.

(21) Appl. No.: 17/590,061

(22) Filed: Feb. 1, 2022

(65) Prior Publication Data

US 2022/0152006 A1 May 19, 2022

Related U.S. Application Data

(63) Continuation of application No. 16/647,995, filed as application No. PCT/PT2018/050035 on Sep. 14, 2018, now Pat. No. 11,273,152.

(51) Int. Cl.
| | | |
|---|---|---|
| A61K 31/445 | (2006.01) |
| A61K 9/06 | (2006.01) |
| A61K 31/4412 | (2006.01) |
| A61K 45/06 | (2006.01) |
| A61K 47/40 | (2006.01) |
| A61P 35/00 | (2006.01) |

(52) U.S. Cl.
CPC .......... *A61K 31/4412* (2013.01); *A61K 9/06* (2013.01); *A61K 45/06* (2013.01); *A61K 47/40* (2013.01); *A61P 35/00* (2018.01)

(58) Field of Classification Search
CPC .............................. A61K 31/445; A61P 35/00
USPC ....................................................... 514/327
See application file for complete search history.

(56) References Cited

U.S. PATENT DOCUMENTS 11,273,152 B2 * 3/2022 Bernardes ........ G01N 33/57492

FOREIGN PATENT DOCUMENTS

| EP | 3156497 A1 | 4/2017 |
| JP | 1996/510232 A | 10/1996 |
| JP | 2013/503888 A | 2/2013 |
| WO | WO 1994/026728 A1 | 11/1994 |
| WO | 2009114126 A1 | 9/2009 |
| WO | WO 2011/028860 A2 | 3/2011 |

OTHER PUBLICATIONS

Aodah, et al., "Preformulation Studies on Piperlongumine", PloS ONE, vol. 11, No. 3, pp. 1-16. (2016).
Cheng, et al., "Novel insights into ion channels in cancer stem cells (Review)", International Journal of Oncology 53, pp. 1435-1441. (2018).
Conde, et al., "Allosteric Antagonist Modulation of TRPV2 by Piperlongumine Impairs Glioblastoma Progression", ACS Central Science, vol. 7. (2021).
Conde, et al., "Allosteric Antagonist Modulation of TRPV2 by Piperlongumine Impairs Glioblastoma Progression", ACS Central Science, vol. 7 (Supporting Information document). pp. 1-51. (2021).
Liu, et al., "Piperlongumine restores the balance of autophagy and apoptosis by increasing BCL2 phosphorylation in rotenone-induced Parkinson disease models", Autophagy, vol. 14, No. 5, 845-861. (2018).
Nabissi, et al., "Cannabidiol stimulates Aml-1a-dependent glial differentiation and inhibits glioma stem-like cells proliferation by inducing autophagy in a TRPV-2 dependent manner", International Journal of Cancer, vol. 137, pp. 1855-1869. (2015).
Olivier, et al., "Drug Resistance in Glioblastoma: The Two Face of Oxidative Stress", Frontiers in Molecular Biosciences, vol. 7, pp. 1-16. (2021).
Tae Hyong Kim, et al. "Piperlongumine treatment inactivates peroxiredoxin 4, exacerbates endoplasmic reticulum stress, and preferentially kills high-grade glioma cells." Neuro-Oncology, vol. 16(10), pp. 1354-1364. (2014), 11 pages.
Xinyao Qiu, et al. "Piperlongumine Inhibits Migration of Glioblastoma Cells via Activation of ROS-Dependent p38 and JNK Signaling Pathways." Hindawi Publishing Corporation, Oxidative Medicine and Cellular Longevity, vol. 2014. (http://dx.doi.org/10.1155/2014/653732). (2014), 13 pages.
Ju Mei Liu, et al. "Piperlongumine selectively kills glioblastoma multiforme cells via reactive oxygen species accumulation dependent JNK and p38 activation." Biochemical and Biophysical Research Communications, vol. 437, pp. 87-93. (2013), 7 pages.
Flávio Rogério Da Nóbrega, et al. "Piplartine Analogues and Cytotoxic Evaluation against Glioblastoma." Molecules, vol. 23, No. 1382. (doi:10.3390/molecules23061382). (2018), 18 pages.
Hasan Turkez, et al. "NFBTA: A Potent Cytotoxic Agent against Glioblastoma." Molecules, vol. 24, No. 2411. (doi:10.3390/molecules24132411). (2019), 26 pages.
M. Alptekin, et al. "Gene expressions of TRP channels in glioblastoma multiforme and relation with survival." International Society of Oncology and BioMarkers. (2015), 5 pages.
C. Bastiancich. "Anticancer drug-loaded hydrogels as drug delivery systems for the local treatment of glioblastoma." Journal of Controlled Release, vol. 243, pp. 29-42. (2016), 14 pages.
Pau Doñate-Macián, et al. "A TRPV2 interactome-based signature for prognosis in glioblastoma patients." Oncotarget, vol. 9, No. 26, pp. 18400-18409. (2018), 10 pages.

(Continued)

*Primary Examiner* — Raymond J Henley, III
(74) *Attorney, Agent, or Firm* — Morgan, Lewis & Bockius LLP

(57) ABSTRACT

This invention relates to the finding that Piperlongumine compounds, such as Piperlongumine and analogues, derivatives and prodrugs thereof, are reversible, allosteric antagonists of transient receptor potential vanilloid 2 channel (TRPV2). Methods of treatment of conditions that are characterised by TRPV2 expression using Piperlongumine compounds and Piperlongumine compounds for use in such treatments are provided.

28 Claims, 18 Drawing Sheets

(56) References Cited

OTHER PUBLICATIONS

Massimo Nabissi, et al. "TRPV2 channel negatively controls glioma cell proliferation and resistance to Fas-induced apoptosis in ERK-dependent manner." Carcinogenesis, vol. 31, No. 5, pp. 794-803. (2010), 10 pages.

Surya Kant Tripathi, et al. "Piperlongumine, a potent anticancer phytotherapeutic: Perspectives on contemporary status and future possibilities as an anticancer agent." Pharmacological Research, vol. 156, No. 104772, pp. 1-18. (2020), 18 pages.

Bezerra, et al. "Piplartine includes inhibition of leukemia cell proliferation triggering both apoptosis and necrosis pathways." Toxicology in VI, Elsevier Science, vol. 21, No. 1, Dec. 8, 2006, pp. 1-8.

International Search Report in International Patent Application No. PCT/PT2018/050035 mailed Sep. 23, 2019.

Bastiancich, et al., "Anticancer drug-loaded hydrogles as drug delivery systems for the local treatment of glioblastoma," *Journal of Controlled Release*, dated Aug. 2016.

Bezerra, et al., "Piplartine induces inhibition of leukemia cell proliferation triggering both apoptosis and necrosis pathways," vol. 21, Issue 1, Feb. 2007, pp. 1-8.

Liberati, et al., "Loss of TRPV2 Homeostatic Control of Cell Proliferation Drives Tumor Progression," (2014), vol. 3, pp. 112-128.

Liu, et al., "Piperlongumine Inhibits Migration of Glioblastoma Cells via Activation of ROS-Dependant p38 and JNK Signaling Pathways," vol. 2014, Article ID 653732, pp. 1-12.

Tominaga, "Molecular mechanisms of thermosensation," Japanese Pharmacological Report, (2014), vol. 124, pp. 219-227.

Yao, et al., "Radio-Sensitization by *Piper longumine* of Human Breast Adenoma MDS-MB-231 Cells in Vitro," Asian Pacific Journal of Cancer Prevention (2014), vol. 15, No. 7, pp. 3211-3217.

Liu, et al., "Piperlongumine conquers temozolomide chemoradiotherapy resistance to achieve immune cure in refractory glioblastoma via boosting oxidative stress-inflamation-CD8+-T cell immunity", Journal of Experiental & Clinical Cancer Research (2023), 42:118, https://doi.org/10.1186/s13046-023-02686-1.

* cited by examiner

TRPV2 ANTAGONISTS

FIELD

This invention relates to the inhibition of the transient receptor potential vanilloid 2 channel (TRPV2) using piperlongumine compounds. This may be useful for example in the treatment of cancer.

BACKGROUND

Natural products (NPs), in particular their fragment-like subset, provide excellent starting points for drug discovery and probes for interrogating biological systems.[1-4] Their biologically pre-validated architectures often comprise scaffolds not covered or only sparingly exploited by fully synthetic chemical matter given the challenging routes for synthesis.[5] Moreover, factual knowledge of target receptors for NPs remains limited and severely hinders the deployment of rational approaches for natural product-inspired molecular design in chemical biology and molecular medicine.[6]

Ligand-centric informatics provides a viable platform to deconvolute phenotypic assay readouts to a macromolecular level. In particular, tools using "fuzzy" pharmacophore descriptors have proven useful for the de-orphanization and target identification in the NP space.[7-10] (−)-Englerin A, a potent anticancer agent[11] and TRP modulator,[12-14] has been recently reported to be a $Ca_v1.2$ antagonist.[15]

Significant efforts have been placed to discover which macromolecular targets are engaged by piperlongumine, since its disclosure as a selective anticancer agent.[16,17] These have recently culminated with a report showing direct inhibition of STAT3.[18] Still, it has been shown that fragment-like NPs may engage multiple targets, resulting in complex polypharmacology networks.[2,9]

SUMMARY

The present inventors have found that the fragment-like anticancer alkaloid piperlongumine (1, FIG. 1A) is a selective allosteric antagonist of the transient receptor potential vanilloid 2 channel (TRPV2) and that the anti-cancer activity of piperlongumine correlates with the expression of TRPV2 in cancer cells.

An aspect of the invention provides a method of treating cancer characterized by transient receptor potential vanilloid 2 channel (TRPV2) expression comprising administering a piperlongumine compound to a patient in need thereof.

Preferred piperlongumine compounds include piperlongumine and analogues, derivatives and prodrugs thereof.

A piperlongumine compound may have the formula 1;

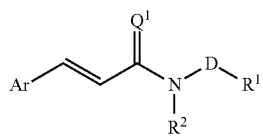

where $Q^1$ is O or S,
—Ar is an optionally substituted aryl group,
-D- is selected from —C(O)—, —C(S)—, —CH(OH)— and —CH(SH)—, and
—$R^1$ and —$R^2$, together with —N-D- to which they are attached, form an optionally substituted heterocyclic ring, or —$R^1$ and —$R^2$ are each independently selected from hydrogen and optionally substituted alkyl, alkenyl, alkynyl, cycloalkyl, heterocyclyl and aryl,
and salts, solvates and protected forms thereof.

Another aspect of the invention provides a piperlongumine compound for use in a method of treating cancer characterized by transient receptor potential vanilloid 2 channel (TRPV2) expression.

Another aspect of the invention provides the use of a piperlongumine compound in the manufacture of a medicament for use in a method of treating cancer characterized by transient receptor potential vanilloid 2 channel (TRPV2) expression.

Aspects and embodiments of the invention are described in more detail below.

against the cannabidiol (CBD)-activated (4 µM) human TRPV2 currents. Wash out of 1 is achieved and full TRPV2 activity can be reinstated; n=2. b) Normalized responses of drug wash out experiment. c) $EC_{50}$ plots for CBD, with increasing concentrations of 1. d) Michaelis-Menten analysis of 1. e) Schild plot for 1.

Figure 4:
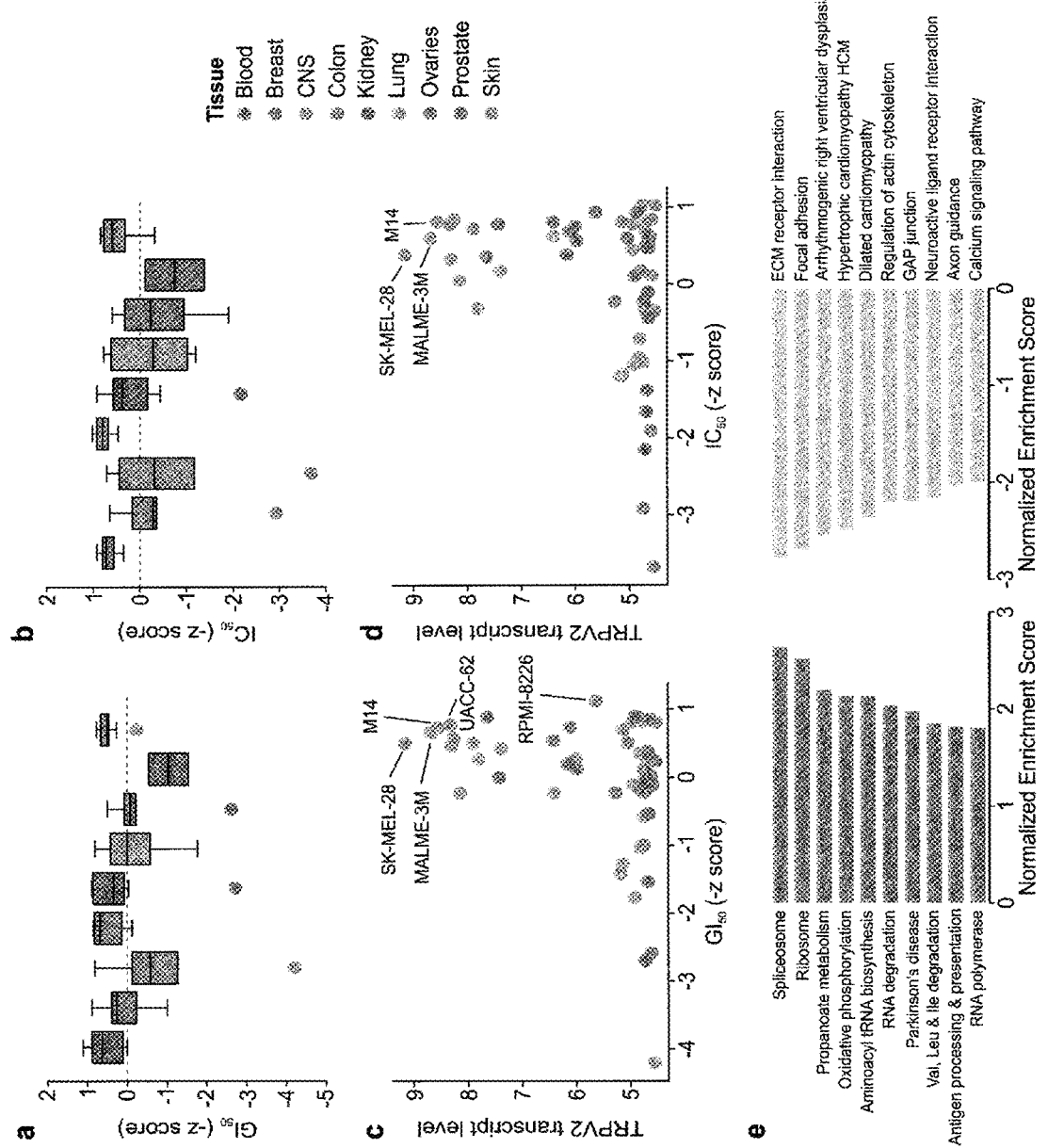

FIG. 4 shows NCI-60 screening and bioinformatics analyses. a) Distribution of piperlongumine, 1, $GI_{50}$ values (-z score) across NCI-60 cancer cell lines, grouped by tissue of origin. Horizontal dashed line represents the panel average. b) Distribution of 1 $IC_{50}$ values (-z score) across NCI-60 cancer cell lines, grouped by tissue of origin. Horizontal dashed line represents the panel average. c) TRPV2 mRNA transcription level (log-intensity) as a function of $GI_{50}$ of 1 (-z scores) across the NCI-60 panel. Cell lines expressing TRPV2 are more sensitive to 1 (Spearman correlation coefficient ($\rho$)=0.28, p<0.05). d) TRPV2 mRNA transcription level (log-intensity) as a function of $IC_{50}$ of 1 (-z scores) across the NCI-60 panel. Cell lines expressing TRPV2 are more sensitive to 1 ($\rho$=0.29, p<0.05). e) Gene Set Enrichment Analysis (GSEA) of genes correlated with activity of 1. GSEA analysis was run on genes ranked according to the Spearman correlation coefficient. With a false discovery rate lower than 5%, 41 gene sets were considered significant. The top 10 gene sets positively (dark grey) and negatively (light grey) correlated with the activity of 1 are shown.

Figure 5:
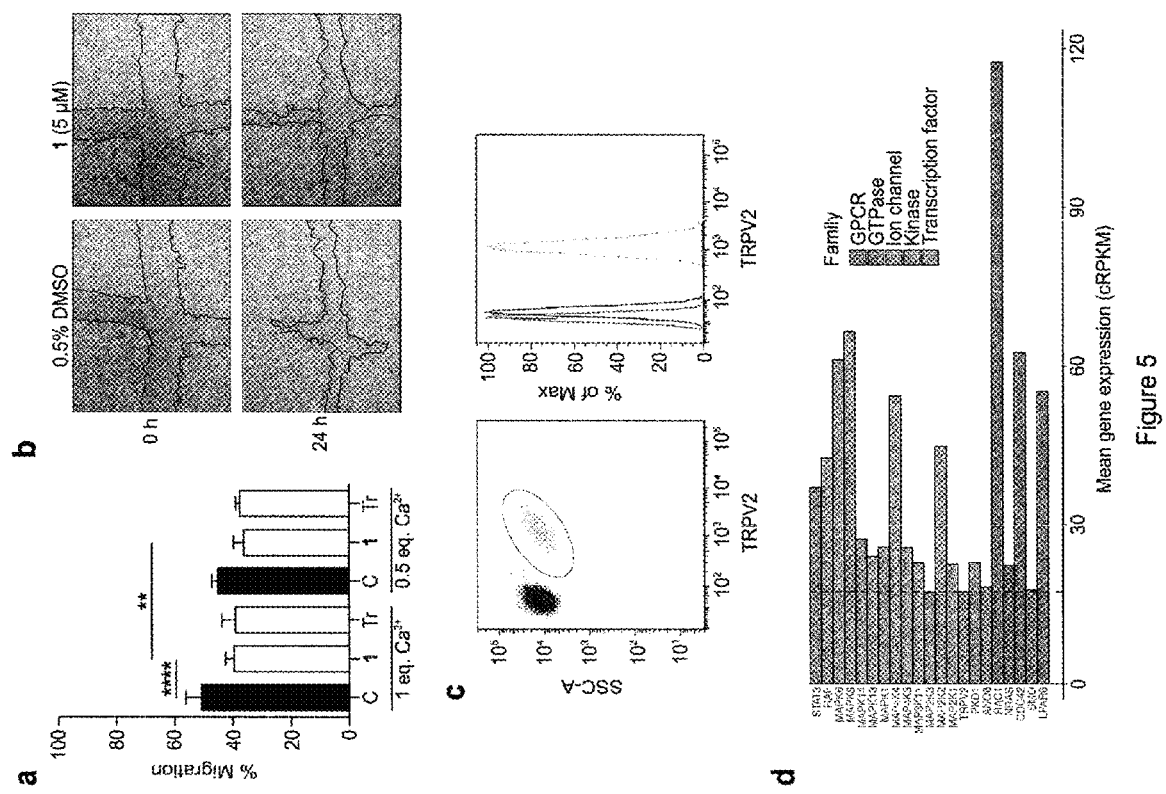

FIG. 5 shows a wound-healing assay with HepG2 cells. a) piperlongumine, 1, inhibits cancer cell migration in a $Ca^{2+}$-dependent manner at a concentration of 5 µM. C—0.5% DMSO control; Tr—tranilast (10 µM). **p<0.0001; p<0.01, unpaired two-tailed t-test. C: n=5-7; 1: n=13-17; Tr: n=4-6. No significant differences were found between DMSO controls. b) Exemplary images of scratches (40×). c) Fluorescence-assisted cell sorting data of HepG2 cells showing constitutive TRPV2 expression. Red: unstained control (mean fluorescence intensity, MFI=5), Blue: Secondary antibody only (MFI=62), Green: Primary and secondary antibody (MFI=1265). d) Analysis of HepG2 RNA-seq data for targets involved in cell migration. From 175 genes tested, there are represented the genes with expression levels equal or higher than TRPV2, colored by gene family. Vertical dashed line represents the TRPV2 expression levels.

Figure 6:
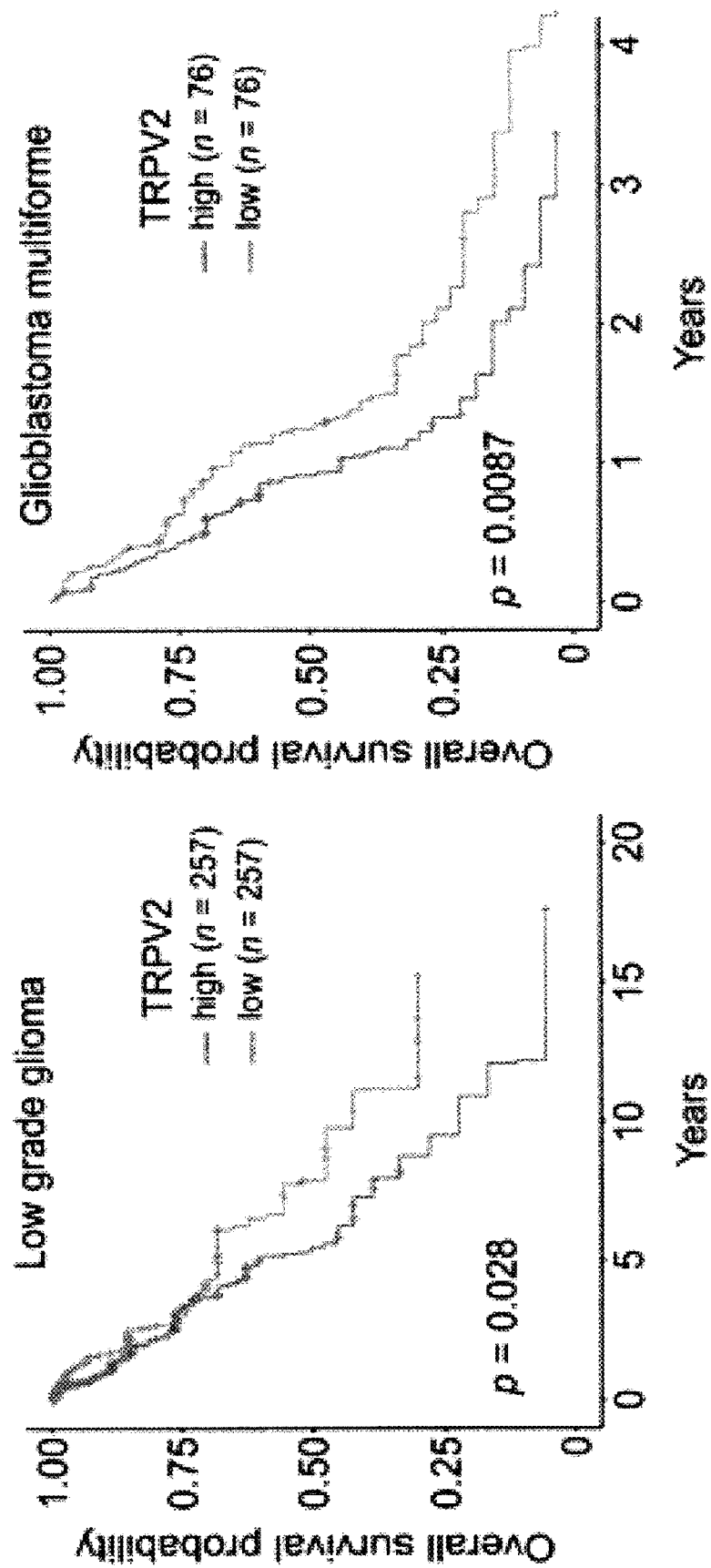

FIG. 6 shows overall survival Kaplan-Meier plots for patient stratification based on hTRPV2 median expression in low-grade glioma and glioblastoma multiforme, indicating that TRPV2 is a prognostic marker in brain tumors. p values for log-rank tests for differences in survival are shown.

Figure 7:
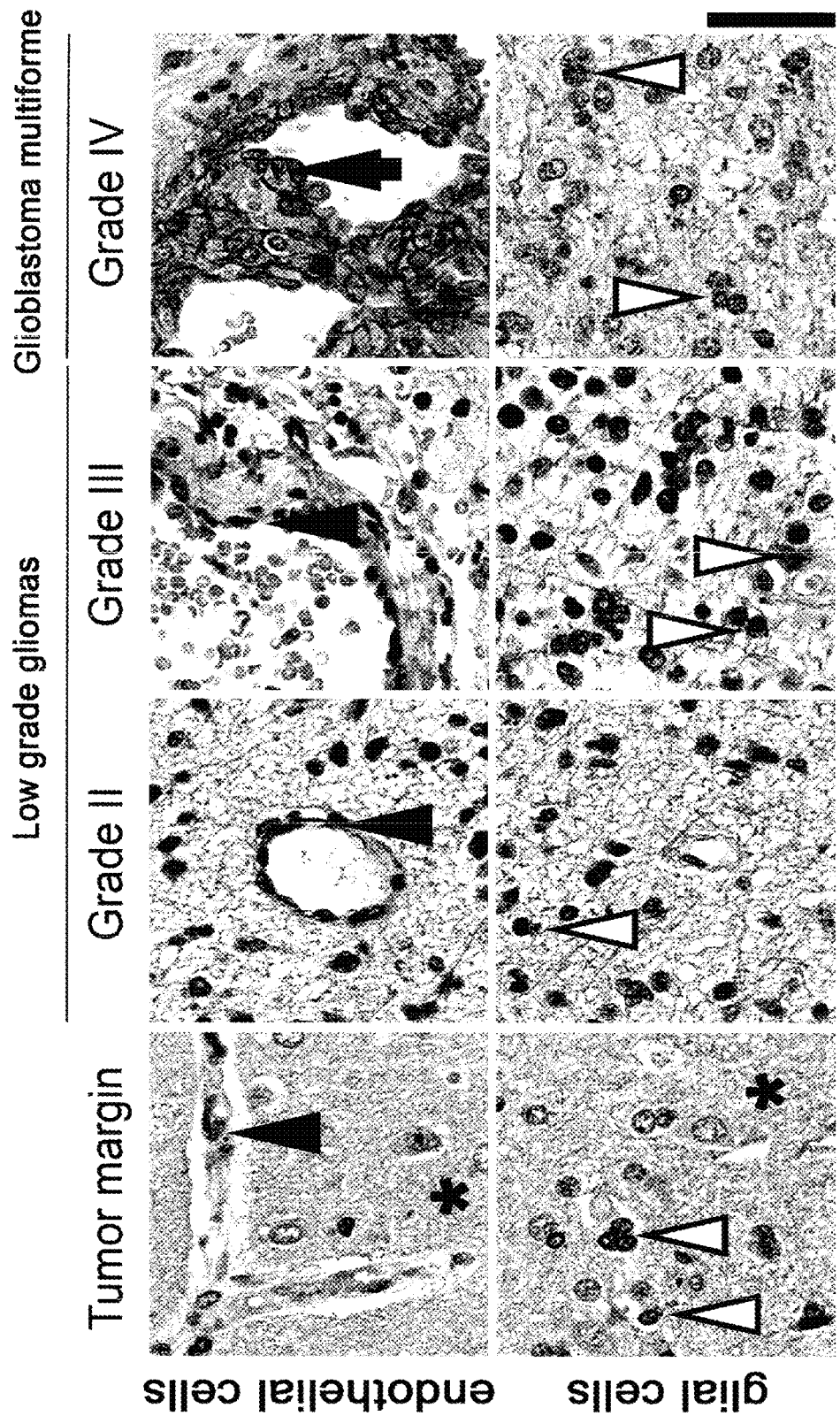

FIG. 7 shows that TRPV2 is expressed in both the glial (white arrowhead) and the endothelial cell compartments (black arrowhead) of human diffuse gliomas, with a clearly distinct level and pattern of expression specifically in endothelial cells of GBM. The intense staining of the cytoplasmic membrane of endothelial cells in GBM contrasts with the weak or negative staining in the endothelium of grade II and III gliomas and with the cytoplasmic and punctate staining in glial cells. TRPV2 expression in normal brain (at tumor margin) in extracellular, diffuse and weak, in the neuropil (asterisk), and punctate in few glial cells (white arrowhead) and neurons.

Figure 8:
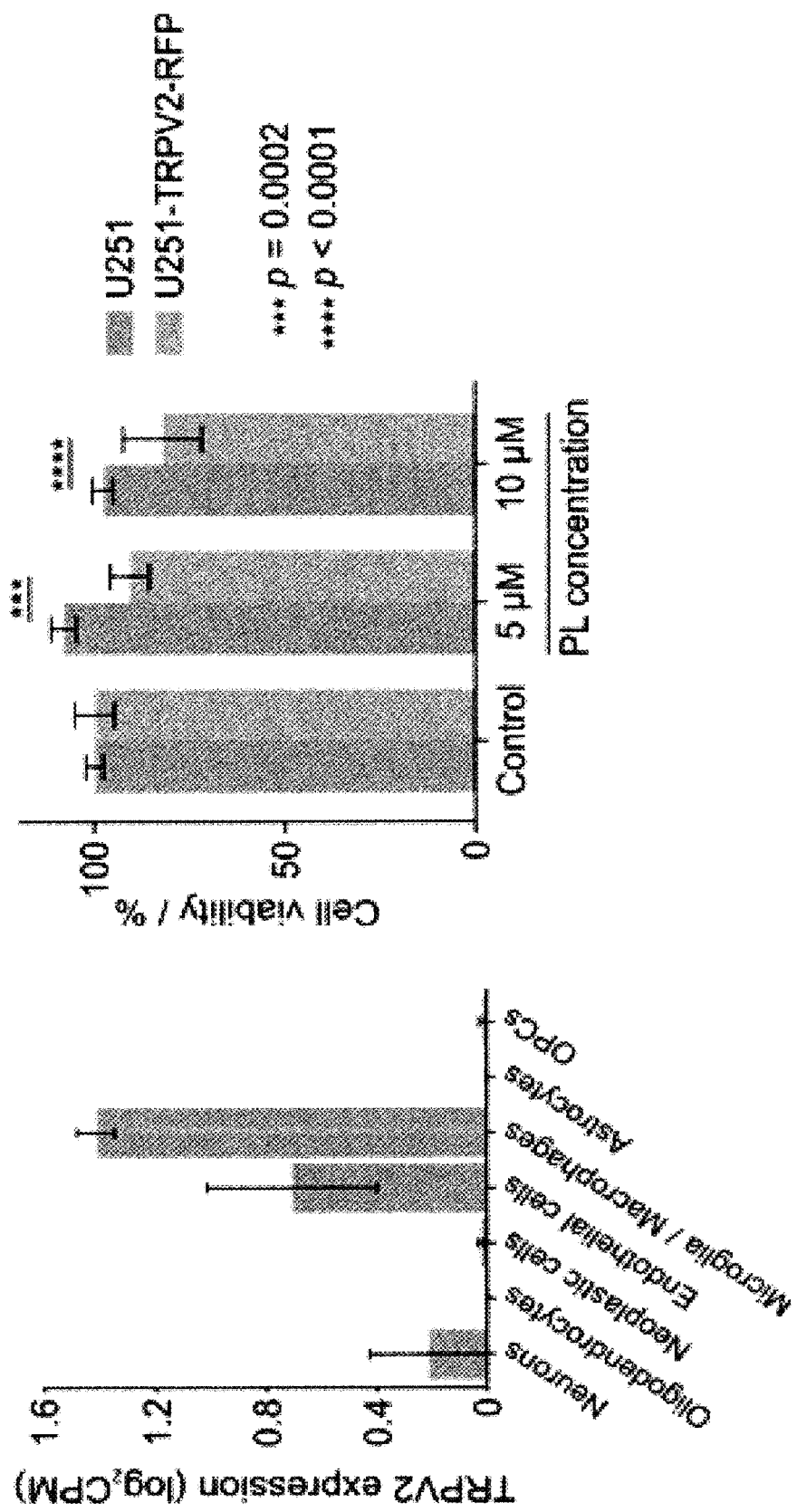

FIG. 8 shows (left panel) that TRPV2 is expressed in endothelial and microglia/macrophage brain tumor cells. TRPV2 expression (log2 of Counts per Million—CPM) across 3,589 single-cells derived from four glioblastoma multiforme human samples, grouped by cell type. Data is shown as mean+/-standard error. FIG. 8 (right panel) shows that transient overexpression of hTRPV2 in U251 cells increases PL toxicity after 24 hours. Results were normalized to transfected cells treated with DMSO vehicle and compared to cells treated with the transfection reagent only, at different concentrations of PL.

Figure 9:
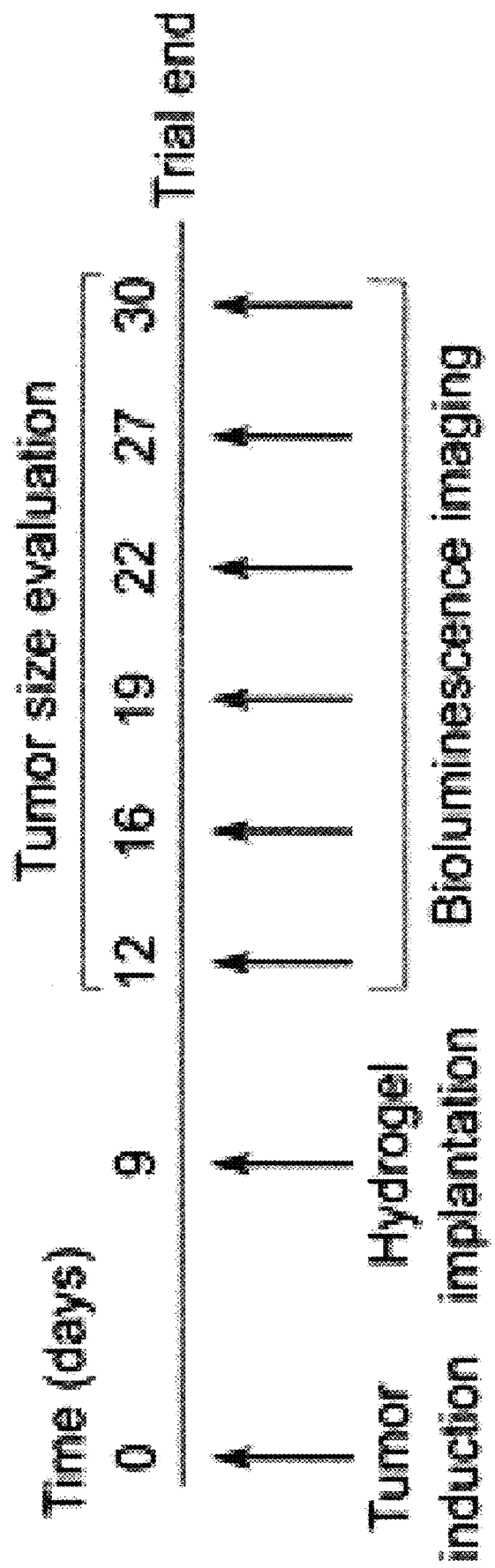

FIG. 9 show the experiment flow for the treatment of glioblastoma multiforme (GBM) in vivo using PL loaded hydrogel: U251 cells were injected intracranially (n=5 per group), 8 days later engraftment was confirmed with bioluminescent imaging. On day nine PL loaded or unloaded hydrogels were implanted. Tumour growth was assessed at regular intervals using bioluminescent imaging.

Figure 10:
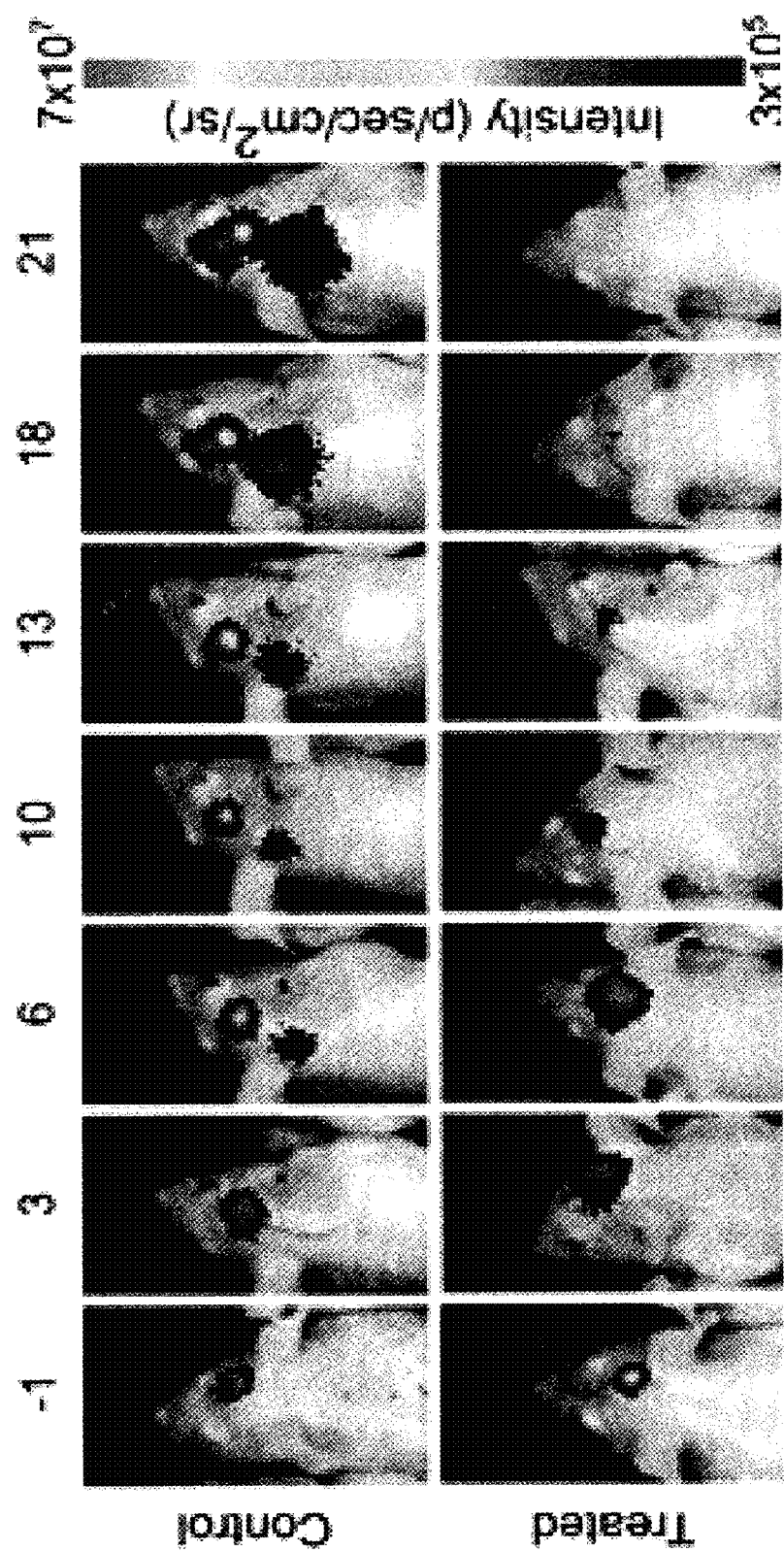

FIG. 10 shows representative bioluminescent images of U251 xenograft mice treated with PL loaded hydrogel (50 mg/kg) or unloaded hydrogel (control), Data shows that PL treatment successfully reduces tumor volume over a period of 21 days compared to the control, in which the tumor grows exponentially.

Figure 11:
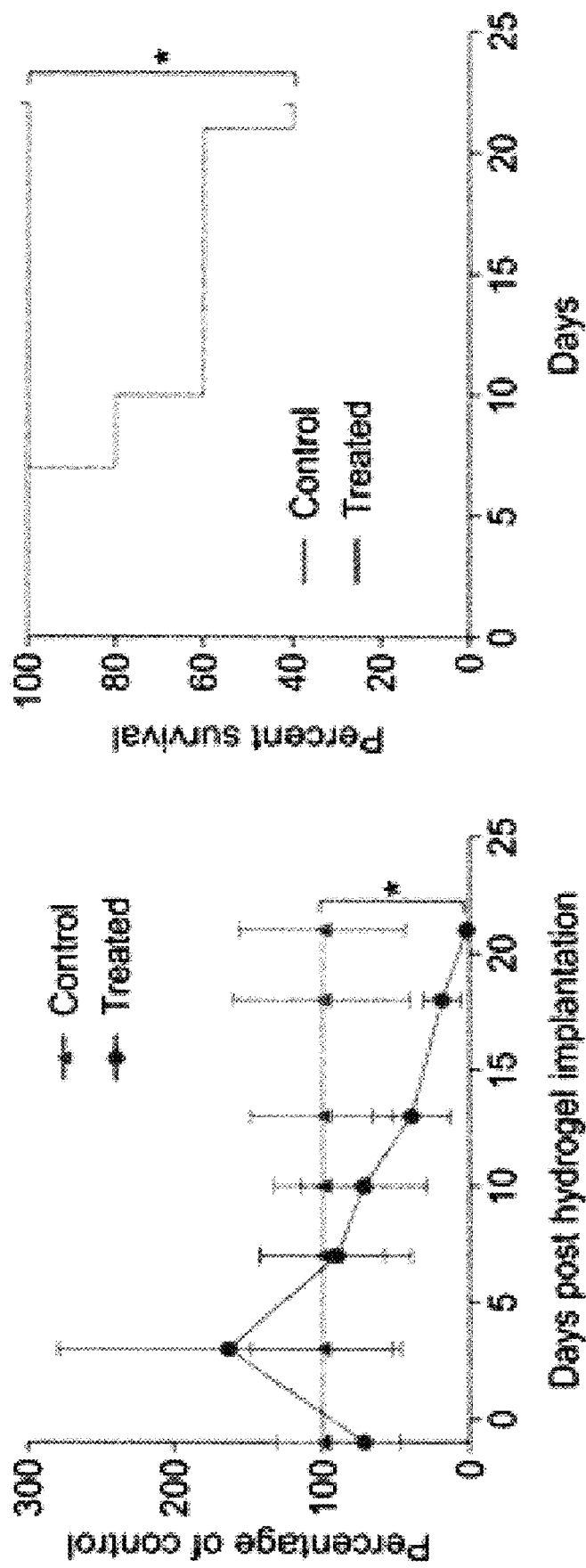

FIG. 11 (left panel) shows tumour burden in mice treated with PL loaded or unloaded hydrogel as measured by luciferase activity. Data expressed as a percentage of the average tumour size in the control group at each time point and represents group mean±SEM. Data shows a significant tumour burden difference between both groups (p=0.0159, n=5, Mann-Whitney test). FIG. 11 also shows (right panel) a Kaplan-Meier survival curve showing that mice treated with PL loaded hydrogels have increased survival (p=0.0494, log-rank (Manel-Cox test) compared to the control group. The survival cut off criteria included an increase in tumour size of 554% compared to the original size measured for each mouse prior to hydrogel implantation.

Figure 12:
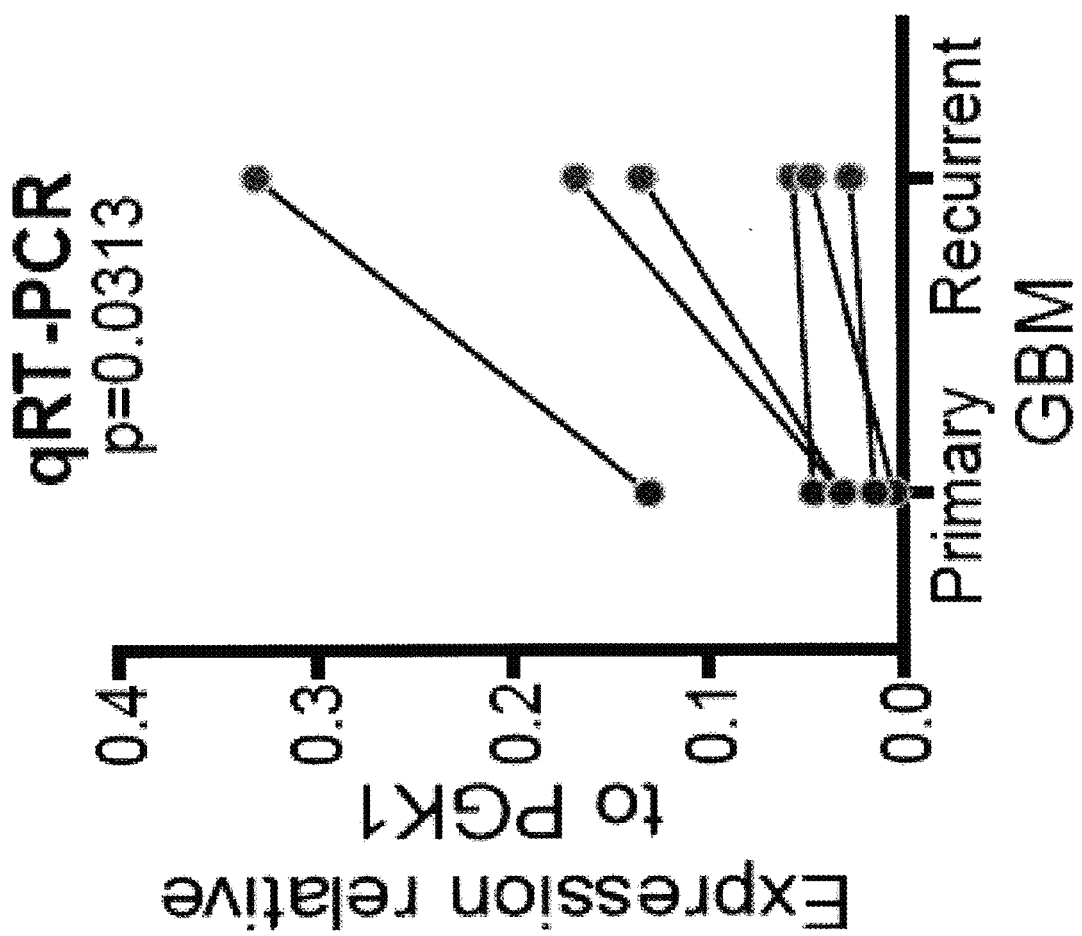

FIG. 12 shows qRT-PCR analysis of the expression of TRPV2 relative to PGK1 in primary and recurrent GBM.

Figure 13:
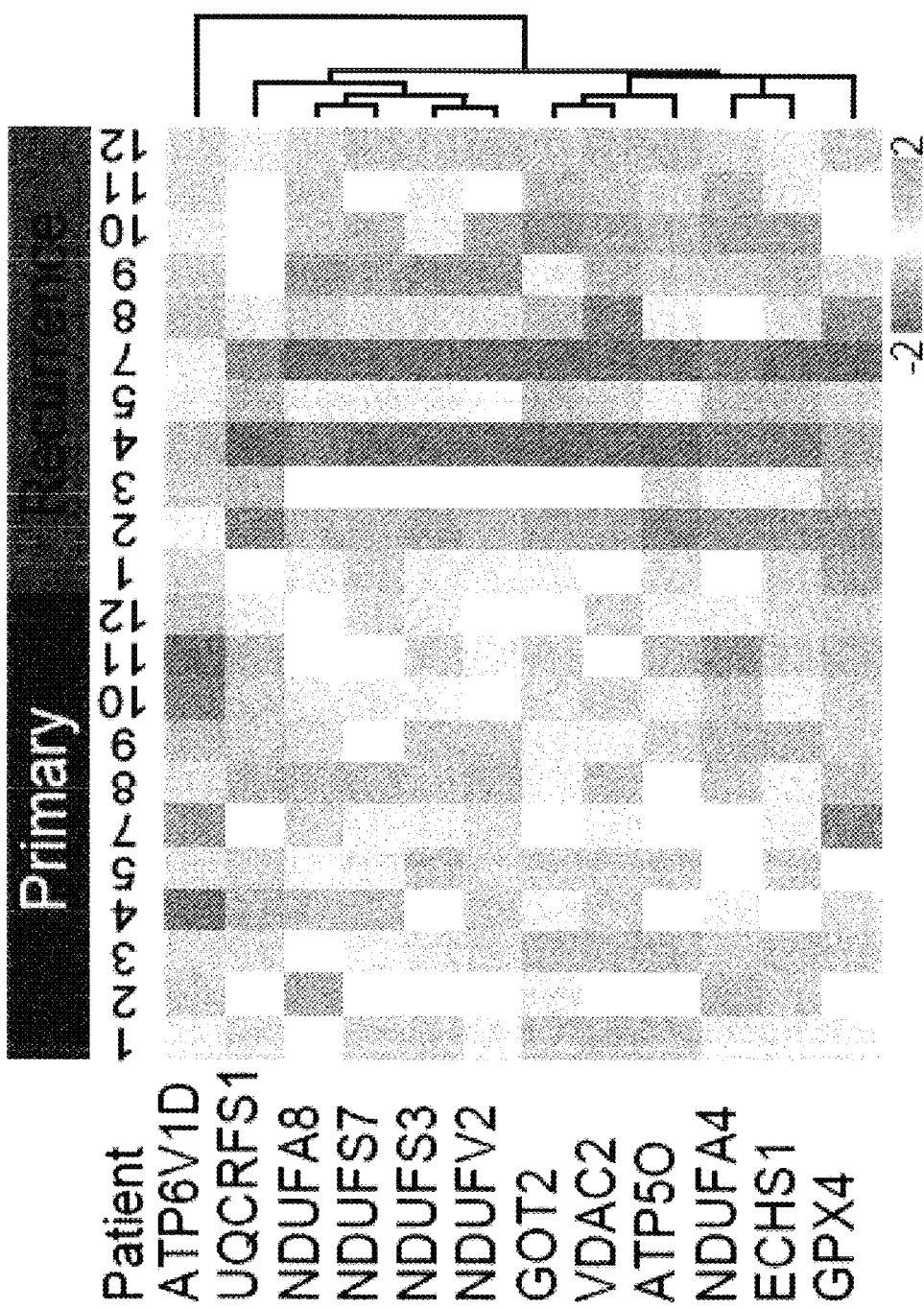

FIG. 13 shows a heatmap for expression of a top ranking geneset (Hallmark Oxidative Phosphorylation) in primary and recurrent GBM.

Figure 14:
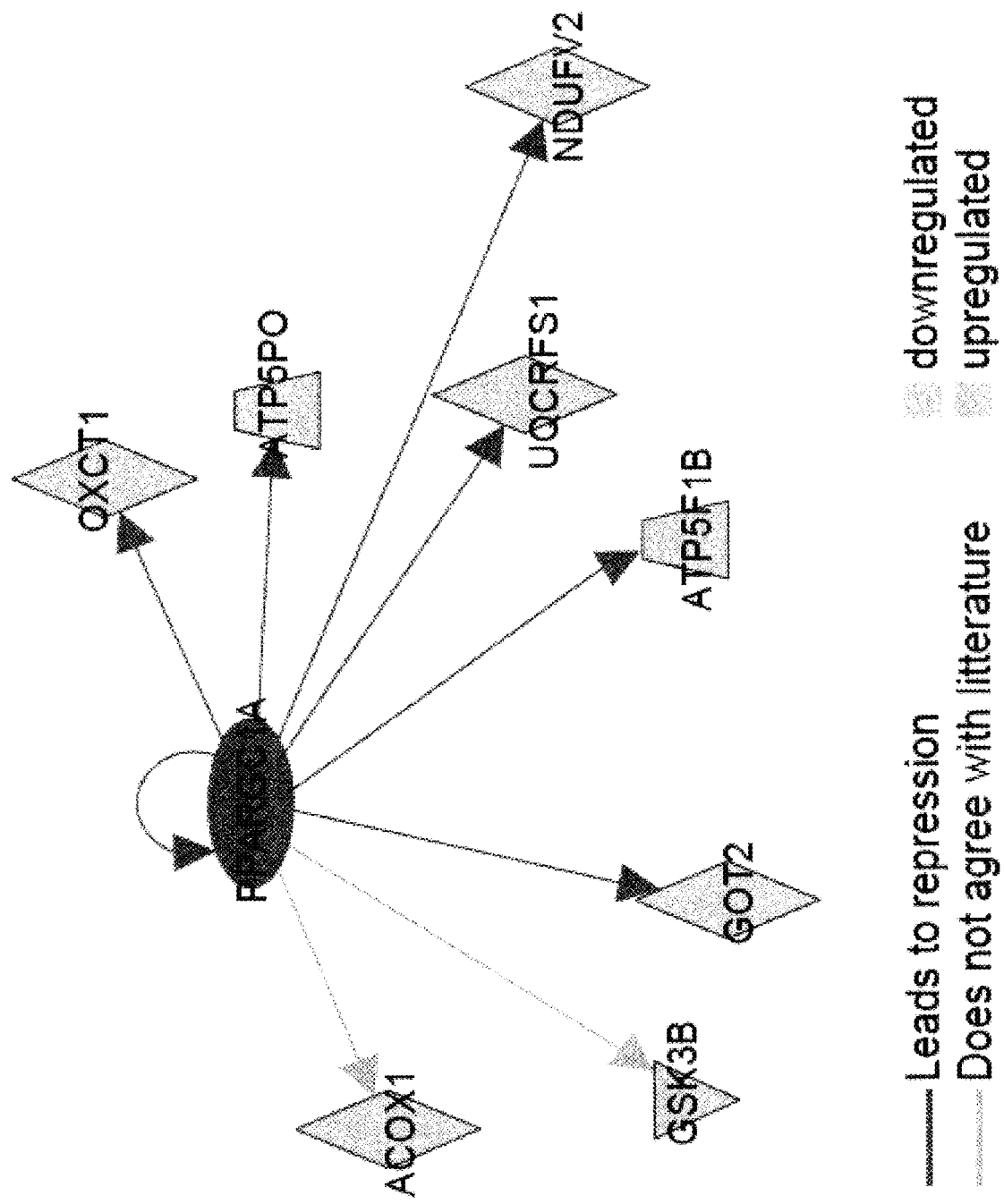

FIG. 14 shows a schematic diagram of the interactions of PPARGC1A.

Figure 15:
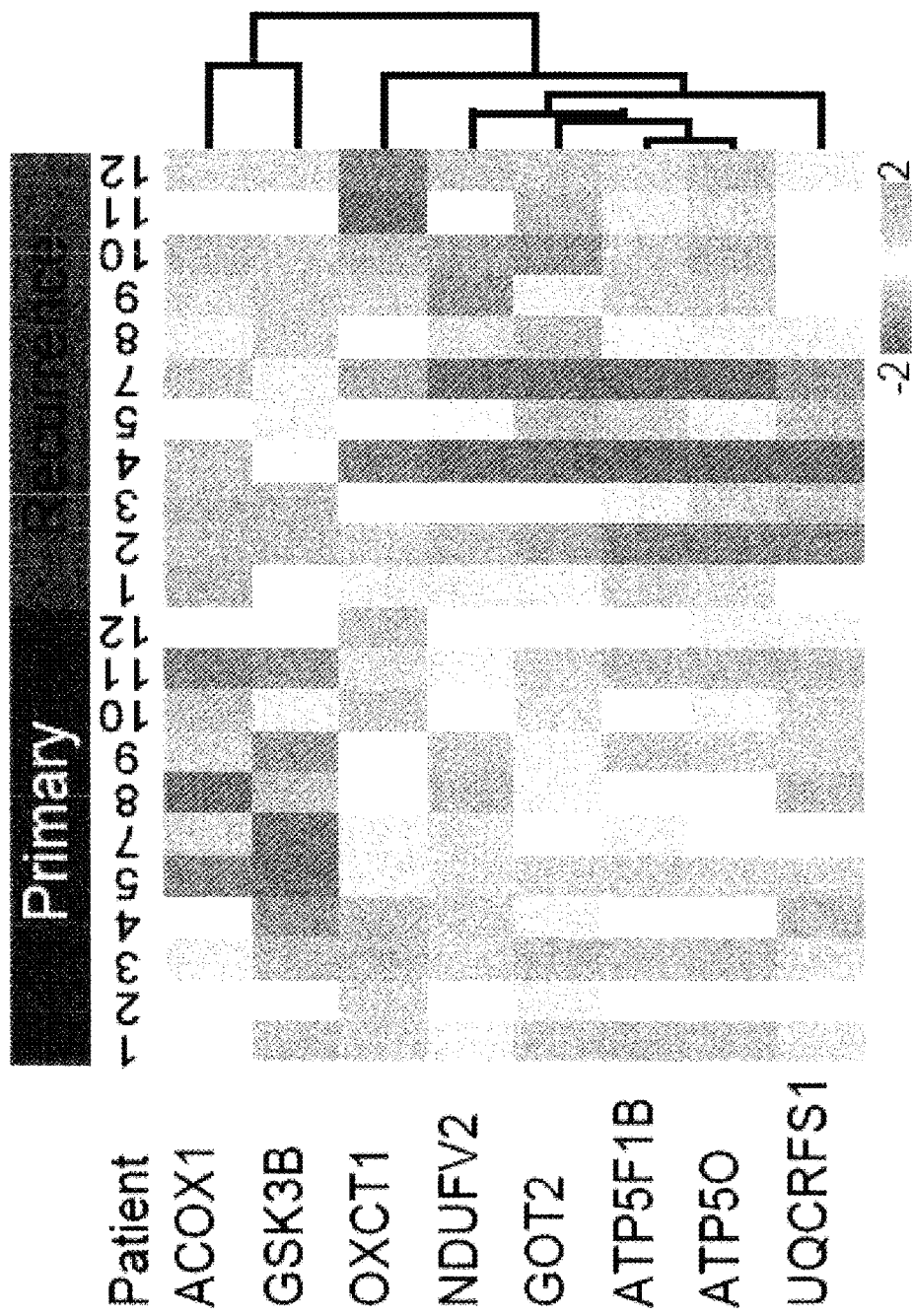

FIG. 15 shows a heatmap for expression of mitochondrial biogenesis genes in primary and recurrent GBM.

Figure 16:
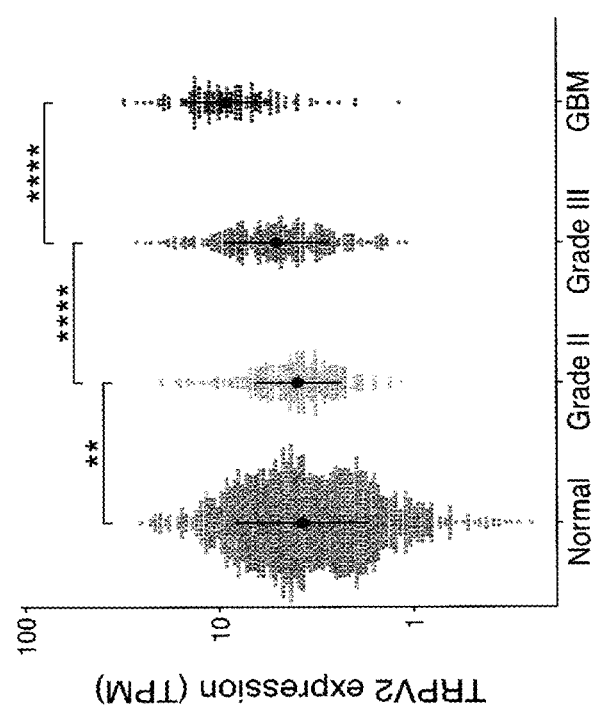

FIG. 16 shows that TRPV2 expression increases concomitantly with brain tumor stage. TRPV2 expression ($log_2$ of TPMs) across GTEx normal and TCGA tumor (grouped in LGG grade II, LGG grade III and GBM) brain samples. Black points and lines represent the median+/-standard deviation. represents p-value<0.01 and **p-value<0.0001 (Wilcoxon rank sum test).

Figure 17:
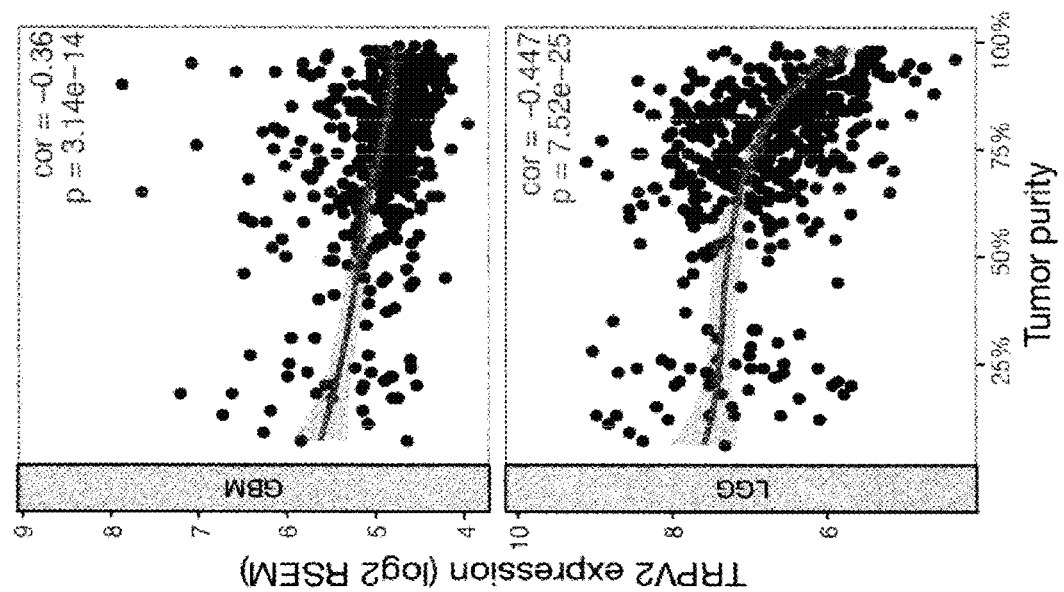

FIG. 17 shows that TRPV2 is mainly expressed in the tumor microenvironment. Scatter plots showing a negative correlation between TRPV2 expression (loge of RSEM) and tumor purity across TCGA GBM and LGG samples (Spearman's correlation coefficient, $\rho$=-0.36 and -0.447, p=3.1× $10^{-14}$ and 7.5×$10^{-25}$, respectively). The grey shade around the blue local polynomial regression (loess) line represents its 95% confidence interval.

DETAILED DESCRIPTION

This invention relates to the finding that piperlongumine compounds are reversible, allosteric antagonists of transient receptor potential vanilloid 2 channel (TRPV2) and may be useful in the treatment of conditions associated with TRPV2 expression.

A piperlongumine compound may inhibit TRPV2, and may preferably be a reversible antagonist of TRPV2. The piperlongumine compound be a selective inhibitor of TRPV2 and may inhibit TRPV2 to a greater extent than other TRP channels. For example, the piperlongumine compound may show at least 5 fold or more, at least 10 fold or at least 100 fold more inhibition of TRPV2 than one or more, preferably all of TRPV1, TRPV3, TRPV4, TRPV5, TRPA1, TRPC1, TRPC3 or TRPC4.

Transient receptor potential vanilloid 2 channel (TRPV2) (also known as VRL and VRL1) is a heat-activated calcium channel. TRPV2 may be human TRPV2. Human TRPV2 (Gene ID 51393) has the reference amino acid sequence of NP_057197.2 and may be encoded by the reference nucleotide sequence NM_016113.4. Techniques for measuring TRPV2 activity and assaying inhibitory activity are described elsewhere herein and include measurement of cannabidiol induced calcium influxes using the Fura2-AM calcium probe.

The piperlongumine compound may have the formula;

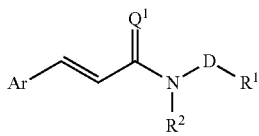

where $Q^1$ is O or S,
—Ar is an optionally substituted aryl group,
-D- is selected from —C(O)—, —C(S)—, —CH(OH)— and —CH(SH)—, and
—$R^1$ and —$R^2$ together with —N-D- to which they are attached, form an optionally substituted heterocyclic ring, or —$R^1$ and —$R^2$ are each independently selected from hydrogen and optionally substituted alkyl, alkenyl, alkynyl, cycloalkyl, heterocyclyl and aryl,
and salts, solvates and protected forms thereof.

The group $Q^1$ is preferably O.

The group —Ar is aryl, including carboaryl or heteroaryl, and the aryl group may be a single aromatic ring or a fused system having two or more aromatic rings.

A carboaryl group may be a $C_{6-14}$ carboaryl group, such as phenyl or naphthyl, and most preferably phenyl.

A heteroaryl group may be a $C_{5-14}$ heteroaryl group, such as a $C_{5-10}$ heteroaryl group, such as a $C_{5-6}$ heteroaryl group, such as a $C_6$ heteroaryl group, such as pyridinyl and pyrimidinyl, or a $C_5$ heteroaryl group, such as furanyl, thiophenyl, and pyrrolyl.

The aryl group may be an aryl group having 6 aromatic ring atoms, such as phenyl or pyridinyl.

Preferably, —Ar is carboaryl, and is most preferably phenyl.

The aryl group may be optionally substituted, such as with one or more substituent groups. The optional substituents may be selected from the group consisting of halo, cyano, —$R^{S1}$, —OH, —$OR^{S1}$, —SH, —$SR^{S1}$, —$NH_2$, —$NHR^{S1}$, —$NR^{S1}R^{S2}$, —COOH, —$CONH_2$, —$CONHR^{S1}$, —$CONR^{S1}R^{S2}$, —$NHCOR^{S1}$, —$N(R^{S1})COR^{S1}$, where each —$R^{S1}$ and each —$R^{S2}$ is independently alkyl, alkenyl, alkynyl, aryl or aralkyl, which are optionally substituted with halo, such as fluoro, or —$R^{S1}$ and —$R^{S2}$ may together form a heterocyclic ring.

The aryl group may be optionally substituted, such as substituted, with one or more groups, such as one, two or three groups.

The aryl group may be optionally substituted with one or more groups selected from —OH, —$OR^{S1}$, —SH, and —$SR^{S1}$, such as —$SR^{S1}$ and —$OR^{S1}$, such as —$OR^{S1}$.

Each —$R^{S1}$ and each —$R^{S2}$ is preferably selected from alkyl, alkenyl, alkynyl, which are each optionally substituted with halo, such as fluoro.

An alkyl, alkenyl or alkynyl group may be linear or branched.

Where —$R^{S1}$ or —$R^{S2}$ is alkyl, this may be $C_{1-6}$ alkyl, such as $C_{1-4}$ alkyl, such as methyl or ethyl, such as methyl.

Where —$R^{S1}$ or —$R^{S2}$ is alkenyl, this may be $C_{2-6}$ alkenyl, such as $C_{2-4}$ alkyl, such as vinyl or allyl.

Where —$R^{S1}$ or —$R^{S2}$ is alkynyl, this may be $C_{2-6}$ alkynyl, such as $C_{2-4}$ alkynyl, such as propargyl.

Where —$R^{S1}$ or —$R^{S2}$ is aryl, this may be carboaryl, such as $C_{6-10}$ aryl, such as phenyl, or heteroaryl, such as a $C_{5-14}$ heteroaryl group, such as a $C_{5-10}$ heteroaryl group, such as a $C_{5-6}$ heteroaryl group, such as a $C_6$ heteroaryl group, such as pyridinyl.

Where —$R^{S1}$ or —$R^{S2}$ is aralkyl, this may be an aryl group, such as described above, connected via a $C_{1-6}$ alkenyl group, such as $C_{1-2}$ alkylene group, such as methylene. The most preferred aralkyl group is benzyl.

Where —$R^{S1}$ and —$R^{S2}$ together form a heterocyclic ring, this may be a $C_{5-7}$ heterocyclic ring, and the heterocyclic ring may optionally contain a further ring heteroatom selected from O, S and N(H).

Where —Ar is a six-membered aryl group this may be substituted at one or more of the 3-, 4- and 5-positions. Here, the 2- and 6-positions may be unsubstituted. In one embodiment, two or each of the 3-, 4- and 5-positions is substituted. Here, the point of connection of the aryl radical is taken as the 1-position.

The group —Ar may be trialkoxy phenyl, such as 3,4,5-trialkoxyphenyl.

The group —Ar may be trimethoxy phenyl, such as 3,4,5-trimethoxyphenyl.

The group -D- is preferably selected from —C(O)— and —C(S)—, and is preferably —C(O)—. Here, the group -D- forms an imide or thioimide together with the nitrogen to which it is attached and —$C(Q^1)$—.

The groups —$R^1$ and —$R^2$, together with —N-D- to which they are attached, form an optionally substituted heterocyclic ring. The heterocyclic ring may be a single ring, or it may be a fused ring system having at least one heterocyclic ring fused to a further ring. The further ring may be another heterocyclic ring, a cycloalkyl ring or an aryl ring.

Preferably the heterocyclic ring is a single ring, and it is not fused to another ring.

The heterocyclic ring may be a 4- to 9-membered ring, such as a 4- to 6-membered ring, such as 5- or 6-membered ring, such as a 6-membered ring.

The heterocycle may contain a further ring heteroatom, which may be selected from O, S and N(H).

Where a further heteroatom is present, this is separated from the nitrogen atom in —N-D- by at least one carbon ring atom. Typically, no further heteroatoms are present, and the remaining ring atoms are carbon ring atoms.

The heterocyclic ring may be saturated, or partially or fully unsaturated. The heterocyclic ring may be an aromatic ring, but this is not preferred.

Preferably, the heterocyclic ring is partially unsaturated. For example, the heterocyclic ring may contain one double bond, which is a carbon-carbon double bond. For the avoidance of doubt the double bond is endo to the heterocycle (that is, within the ring). Where the group -D- is —C(O)— or —C(S)— it is preferred that the double bond is conjugated with the group -D-.

The heterocyclic ring is a lactam when -D- is —C(O)— or —C(S)—. This is preferred.

The lactam may be partially or fully unsaturated. The lactam may be α,β-unsaturated, and may be further γ,δ-unsaturated where a second double bond is present.

Preferably, —R$^1$ and —R$^2$, together with —N-D- to which they are attached, form an α,β-unsaturated δ-lactam (5,6-dihydropyridin-2-one-1-yl).

Alternatively, —R$^1$ and —R$^2$, together with —N-D- to which they are attached, form an α,β-unsaturated δ-lactam.

The heterocyclic ring formed by R$^1$ and —R$^2$ together with —N-D- may be optionally substituted, such as optionally substituted with alkyl or halo, such as alkyl. Preferably, the heterocyclic ring is not further substituted.

Alternatively, each of —R$^1$ and —R$^2$ is independently selected from hydrogen, alkyl, alkenyl, alkynyl, and optionally substituted cycloalkyl, heteroalkyl, heterocyclyl and aryl. Preferably one of —R$^1$ and —R$^2$ is not hydrogen. For example, —R$^2$ may be hydrogen, whilst —R$^1$ is other than hydrogen. Both of —R$^1$ and —R$^2$ may not be hydrogen.

The cycloalkyl, heteroalkyl, heterocyclyl and aryl groups may be optionally substituted with alkyl, such as $C_{1-6}$ alkyl, such as methyl.

The group —R$^1$ may be alkyl or alkenyl, for example when —R$^2$ is hydrogen.

Where —R$^1$ or —R$^2$ is an alkyl group, this may be a straight or branched alkyl group, such as a $C_{1-10}$ alkyl group, such as a $C_{1-6}$, such as a $C_{1-4}$ alkyl group, such as $C_{1-2}$ alkyl. Examples include methyl, ethyl and propyl.

Where —R$^1$ or —R$^2$ is an alkenyl group, this may be a straight or branched alkenyl group having one or more, preferably one carbon-carbon double bond, such as a $C_{2-10}$ alkenyl group, such as a $C_{2-6}$ alkenyl group, such as a $C_{2-4}$ alkenyl group. Examples include vinyl and allyl.

Where —R$^1$ or —R$^2$ is an alkynyl group, this may be a straight or branched alkynyl group having one or more, preferably one carbon-carbon triple bond, such as a $C_{2-10}$ alkynyl group, such as a $C_{2-6}$ alkynyl group, such as a $C_{2-4}$ alkynyl group. An example is propargyl.

A reference to a cycloalkyl group, this may be a cyclic alkyl group such as $C_{3-7}$ cycloalkyl group, such as a $C_{5-6}$ cycloalkyl group. The cycloalkyl group may be saturated, or partially or fully saturated, but it is not aromatic. An example is cyclohexyl.

Where —R$^1$ or —R$^2$ is an heteroalkyl group, this may be an alkyl group where one or two of the carbon atoms is replaced with a heteroatom selected from O, S and N(H). The heteroalkyl group may be linear or branched, and may be a $C_{2-10}$ heteroalkyl group, such as $C_{2-6}$ heteroalkyl group, such as $C_{2-4}$ heteroalkyl group. The heteroalkyl group may be connected via a carbon atom, or a nitrogen atom, where present. An example is methoxymethyl.

Where —R$^1$ or —R$^2$ is an heterocyclyl group, this may be a cyclic heterocyclic group having one or two heteroatoms each independently selected from O, S and N(H). The heterocyclyl group may be a $C_{3-10}$ heterocyclyl group, such as a $C_{5-7}$ heterocyclyl group, such as a $C_{5-6}$ heterocyclyl group. The heterocyclic group may be saturated, or partially or fully saturated, but it is not aromatic. The heterocyclyl group may be connected via a carbon ring atom, or a nitrogen ring atom, where present. The heterocyclic group may be pyrrolidinyl, morpholinyl and piperidinyl.

Where —R$^1$ or —R$^2$ is an aryl group this may be an aromatic group that may be carboaryl or heteroaryl. The carboaryl group may be phenyl or naphthyl. The heteroaryl group may be $C_{5-10}$ heteroaryl, such as $C_{5-6}$ heteroaryl. Examples include pyridinyl, imidazoyl and thiazoyl.

The compound may be provided as a solvate, such as a hydrate.

The compound may be provided in salt form, where appropriate, for example where carboxy (—COOH) or amino (such as —NH— or —NH$_2$) functionality is present within the compound.

The compound may be provided as a protected from, where appropriate. For example where amino functionality (such as —NH— or —NH$_2$) is present this may be protected with a carbamate group, such as a Boc group, and where hydroxyl functionality (—OH) is present this may be protected with a silyl group, such as TBDMS. The use of protecting groups is well known in the art and the skilled person can appreciate that other functionality may be protected, where required, and other protecting groups may be used, as required.

Tautomers of the compounds of formula 1 are also within the scope of the invention.

Prodrug forms of the compound of formula 1 are also within the scope of the invention. For example, where the compound has carboxy (—COOH) or hydroxy (—OH) functionality, these groups may be provided in ester form, where such esters are labile under physiological conditions.

The piperlongumine compound may be piperlongumine or an analogue, derivative or prodrug of piperlongumine. Piperlorigumine (CAS 20069-09-04) may be obtained from commercial suppliers, synthesised using standard techniques or isolated from the *Piper longum* plant in accordance with standard methods. For example, Seo et al. (*Bioorg. Med. Chem. Lett.* 2014, 24, 5727) describe the preparation of piperlongumine derivatives.

In the compound of formula 1, piperlongumine is a compound where Q$^1$ is O, —Ar is 3,4,5-triemethoxyphenyl, and —R$^1$ and —R$^2$, together with —N-D- to which they are attached, form an α,β-unsaturated δ-lactam (5,6-dihydropyridin-2-one-1-yl).

A patient suitable for treatment as described herein may have cancer that is characterized by TRPV2 expression. Cancer suitable for treatment as described herein may be any type of solid or non-solid cancer or malignant lymphoma and especially leukaemia, sarcomas, skin cancer, bladder cancer, breast cancer, uterine cancer, ovarian cancer, prostate cancer, lung cancer, colorectal cancer, cervical cancer, liver cancer, head and neck cancer, oesophageal cancer, pancreatic cancer, renal cancer, stomach cancer and cerebral cancer. Cancers may be familial or sporadic. In some preferred embodiments, the cancer may be a skin cancer, breast cancer, prostate cancer, brain cancer, such as glioma or glioblastoma, or blood cancer.

In some especially preferred embodiments, the cancer may be a brain cancer, such as a glioma for example grade II glioma (diffuse astroglioma or astrocytoma), grade III gliomer (anaplastic astoglioma or astrocytoma) or grade IV glioma (glioblastoma), for example glioblastoma multiforme (GBM). The gliomer may be low or high grade gliomer.

Glioblastoma may be primary or recurrent glioblastoma.

The cancer may be a metastatic cancer.

Cancer characterized by TRPV2 expression may comprise one or more cancer cells in the patient that have increased expression of TRPV2 relative to control cells. For example, the expression of TRPV2 in one or more cancer cells in the patient may be greater than the expression in a control cell or greater than a predetermined threshold value.

A cancer characterized by TRPV2 expression may be identified by any suitable technique. For example, the expression of TRPV2 in one or more cancer cells from the patient may be determined. Suitable techniques for determining the expression of target genes in a cell are well-known in the art and include PCR-based methods, such as reverse transcription PCR (RT-PCR), quantitative RT-PCR (qPCR), TaqMan™, or TaqMan™ low density array (TLDA), microarrays, multi-analyte profile testing, radio-immunoassay (RIA), northern blot assay, Western blot assay, immunofluorescent assay, enzyme immunoassay, enzyme linked immunosorbent assay (ELISA), immunoprecipitation assay, chemiluminescent assay, immunohistochemical assay, dot blot assay, or slot blot assay or proteomics-based methods. In some embodiments, a cancer characterized by TRPV2 expression may be identified by immunohistochemistry.

The patient may have been previously identified as having cancer characterized by TRPV2 expression or be at risk of having or at risk of a cancer characterized by TRPV2 expression.

A method may comprise identifying the patient as having or at risk of a cancer characterized by TRPV2 expression before administration.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or leporid) may be employed.

In some embodiments, the individual may have minimal residual disease (MRD) after an initial cancer treatment.

An individual with a cancer characterized by TRPV2 expression may display at least one identifiable sign, symptom, or laboratory finding that is sufficient to make a diagnosis of a cancer characterized by TRPV2 expression in accordance with clinical standards known in the art. Examples of such clinical standards can be found in textbooks of medicine such as Harrison's Principles of Internal Medicine, 15th Ed., Fauci AS et al., eds., McGraw-Hill, New York, 2001. In some instances, a diagnosis of a cancer in an individual may include identification of a particular cell type (e.g. a cancer cell) in a sample of a body fluid or tissue obtained from the individual. In some embodiments, the individual may have been previously identified or diagnosed with cancer characterized by TRPV2 expression or a method of the invention may comprise identifying or diagnosing cancer characterized by TRPV2 expression in the individual for example by determining the presence of an identifiable sign, symptom, or laboratory finding indicative of cancer characterized by TRPV2 expression in the individual.

While it is possible for a piperlongumine compound, such as piperlongumine, to be administered to the individual alone, it is preferable to present the compound in a pharmaceutical composition or formulation.

A pharmaceutical composition may comprise, in addition to the piperlongumine compound, one or more pharmaceutically acceptable carriers, adjuvants, excipients, diluents, fillers, buffers, stabilisers, preservatives, lubricants, or other materials well-known to those skilled in the art. Such materials should be non-toxic and should not interfere with the efficacy of the active compound. The precise nature of the carrier or other material will depend on the route of administration, which may be by bolus, infusion, injection or any other suitable route, as discussed below. Suitable materials will be sterile and pyrogen free, with a suitable isotonicity and stability. Examples include sterile saline (e.g. 0.9% NaCl), water, dextrose, glycerol, ethanol or the like or combinations thereof. The composition may further contain auxiliary substances such as wetting agents, emulsifying agents, pH buffering agents or the like.

Suitable carriers, excipients, etc. can be found in standard pharmaceutical texts, for example, Remington's Pharmaceutical Sciences, 18th edition, Mack Publishing Company, Easton, Pa., 1990.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well-known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

The piperlongumine compound or pharmaceutical compositions comprising the piperlongumine compound may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Usually administration will be by the oral route, although other routes such as intraperitoneal, subcutaneous, transdermal, intravenous, nasal, intramuscular or other convenient routes are not excluded.

The pharmaceutical compositions comprising the piperlongumine compounds may be formulated in a dosage unit formulation that is appropriate for the intended route of administration.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, ascorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example, from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

In some embodiments, a piperlongumine compound described herein may be encapsulated, for example in a cyclic oligosaccharide, such as cyclodextrin. The encapsulated piperlongumine compound may be contained in a hydrogel, for example for use as a post-surgical implant.

Optionally, other therapeutic or prophylactic agents may be included in the pharmaceutical composition or formulation.

Piperlongumine compounds as described herein is useful in the treatment of cancer, for example cancers characterized by TRPV2 expression.

Treatment may be any treatment or therapy, whether of a human or an animal (e.g. in veterinary applications), in which some desired therapeutic effect is achieved, for example, the inhibition or delay of the onset or progress of the condition, and includes a reduction in the rate of progress, a halt in the rate of progress, inhibition of metastasis, amelioration of the condition, cure or remission (whether partial or total) of the condition, preventing, delaying, abating or arresting one or more symptoms and/or signs of the condition or prolonging survival of a subject or individual beyond that expected in the absence of treatment.

Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens. Inhibition of TRPV2 in an individual with cancer, as described herein may improve the capacity of the individual to resist cancer growth, in particular growth of a cancer already present the subject and/or decrease the propensity for cancer growth in the individual.

Treatment as described herein may include prophylactic treatment (i.e. prophylaxis) i.e. the individual being treated may not have or may not be diagnosed as having a cancer characterised by TRPV2 expression at the time of treatment. For example, an individual susceptible to or at risk of the occurrence or re-occurrence of a cancer characterised by TRPV2 expression may be treated as described herein. Such treatment may prevent or delay the occurrence or re-occurrence of the cancer characterised by TRPV2 expression in the individual or reduce its symptoms or severity after occurrence or re-occurrence. In some embodiments, the individual may have been previously identified as having increased susceptibility or risk of cancer characterised by TRPV2 expression compared to the general population or a method may comprise identifying an individual who has increased susceptibility or risk of cancer characterised by TRPV2 expression. Prophylactic or preventative treatment may be preferred in some embodiments.

Piperlongumine compounds may be administered as described herein in therapeutically-effective amounts.

The term "therapeutically-effective amount" as used herein, pertains to that amount of an active compound, or a combination, material, composition or dosage form comprising an active compound, which is effective for producing some desired therapeutic effect, commensurate with a reasonable benefit/risk ratio.

The appropriate dosage of a piperlongumine compounds may vary from individual to individual. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the individual. The amount of active compounds and route of administration will ultimately be at the discretion of the physician, although generally the dosage will be to achieve therapeutic plasma concentrations of the active compound without causing substantial harmful or deleterious side-effects.

In general, a suitable dose of the active compound is in the range of about 100 µg to about 400 mg per kilogram body weight of the subject per day, preferably 200 µg to about 200 mg per kilogram body weight of the subject per day. Where the active compound is a salt, an ester, prodrug, or the like, the amount administered is calculated on the basis of the parent compound and so the actual weight to be used is increased proportionately. For example, 50 to 100 mg of piperlongumine compound may be orally administered twice daily in capsule or tablet form.

A piperlongumine compound may be orally administered in an amount sufficient to maintain the serum concentration at a level that yields >50% inhibition of TRVP2.

Administration in vivo can be effected in one dose, continuously or intermittently (e.g., in divided doses at appropriate intervals).

Methods of determining the most effective means and dosage of administration are well known in the art and will vary with the formulation used for therapy, the purpose of the therapy, the target cell being treated, and the subject being treated. Single or multiple administrations can be carried out with the dose level and pattern being selected by the physician.

Multiple doses of the piperlongumine compound may be administered, for example 2, 3, 4, 5 or more than 5 doses may be administered. The administration of the piperlongumine compound may continue for sustained periods of time. For example treatment with the piperlongumine compound may be continued for at least 1 week, at least 2 weeks, at least 3 weeks, at least 1 month or at least 2 months. Treatment with the piperlongumine compound may be continued for as long as is necessary to reduce cancer symptoms or achieve complete remission.

The piperlongumine compound may be administered alone or in combination with other treatments, either simultaneously or sequentially dependent upon the individual circumstances. For example, a piperlongumine compound as described herein may be administered in combination with one or more additional active compounds.

The piperlongumine compound may be administered in combination with a second therapeutic agent.

The second therapeutic agent may be an anti-cancer compound, for example, an anti-cancer compound is selected from an anthracycline, cytarabine, vincristine, L-asparaginase, cyclophosphamide, fibromun, dacarbazine, methotrexate and 6-mercaptopurine, chlorambucil, an alkylating agent, cyclophosphamide, corticosteroids, imatinib, cladribine, pentostatin, rituximab, chlorambucil, a taxane, and doxorubicin.

The piperlongumine compound may be administered in combination with irradiation. The use of irradiation for the treatment of cancer conditions is well known in the art.

The expression of TRPV2 may also be useful in identifying cancers that are that are likely to be responsive ("sensitive") or non-responsive ("resistant") to treatment with a piperlongumine compound and to selecting patients suitable for treatment with a piperlongumine compound. A method of selecting a cancer patient for treatment with a piperlongumine compound comprising
  providing a sample of cancer cells from a cancer patient, and
  determining the presence or amount of TRPV2 expression in the cancer cells.

A cancer patient with cancer cells that express TRPV2; express TRPV2 at a level above a threshold value or at higher levels than a control cell may be selected for treatment with the piperlongumine compound. Techniques suitable for determining the presence or amount of expression of TRPV2 in cells are well-known in the art.

A patient may have a cancer as described above, for example a brain cancer, such as glioblastoma.

The present inventors have also identified a correlation between TRPV2 expression and poor prognosis in cancer patients (e.g. a survival rate of less than 50% over 3 years), in particular patients with brain cancers such as glioblastoma.

Another aspect of the invention provides a method of prognosis of a cancer patient comprising
  providing a sample of cancer cells from a cancer patient, and,
  determining the amount of TRPV2 expression in the cancer cells, the level of TRPV2 expression being indicative of the prognosis of the patient.

The patient may have a cancer as described above, for example a brain cancer, such as glioblastoma.

The amount of expression of TRPV2 in the cancer cells may be determined using any suitable technique.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

EXPERIMENTS

Methods

Target Prediction

Target predictions with SPiDER were carried out on the publically available web server (www.modlabcadd.ethz.ch/software/spider) as previously reported.[2,11,14,20] In short, piperlongumine was projected onto self-organizing maps together with reference compounds from the COBRA database.[31] Chemical structures are processed with the "wash" function of the Molecular Operating Environment (MOE, Chemical Computing Group, Montreal, Canada), prior to description with the CATS2[32] and MOE2D descriptors. Predictions are carried out by calculating the Euclidean distances of the molecules to the reference compounds in COBRA. The output comprises target families at a confidence level of $p<0.05$. The distances are converted to p values, according to a pre-calculated background distribution of distances between molecules annotated to bind different targets. The arithmetic average of these p values serves as confidence score for the target prediction. With the background distribution of confidence scores, each prediction can be associated with another p value that indicates the statistical significance of the prediction.[14]

t-Distributed Stochastic Neighborhood Embedding (t-SNE).

Ligands annotated to human transient receptor potential (TRP) channels were collected from ChEMBL23[33] and filtered as previously described. The CATS2 descriptors[32] and the ECFP4-like Morgan fingerprints (radius 2, 2048 bits) were calculated for all TRP ligands and piperlongumine using MOE2018 (Chemical Computing Group, Canada) and RDKit, respectively. Principal component analyses were performed for the CATS2 descriptors and expanded fingerprints, individually. The principal components describing at least 80% of data variance were kept for manifold learning. For t-SNE, principal components were scaled prior to probabilistic analyses (1000 iterations and learning rate of 600-1000). The analyses were carried out in Python 2.7.13 using the Num Py 1.13.3, Pandas 0.21.0 and Scikit-learn 0.18.1 libraries. Plots were computed with Matplotlib 1.5.3.

Fluorescence Cell-Based Assays

The assays were performed at SB Discovery (Glasgow, UK) on a fee-for-service basis. Human TRP cells were trypsinised, counted and seeded in black, clear-bottomed 96 well plates at a density of 50,000 cells per well in 100 μL volume and incubated overnight. Next day, the cells were loaded with calcium 5 dye or membrane potential dye. TRPV1-5, TRPA1, TRPM2, TRPM3, and TRPM8 were tested using the calcium 5 dye. TRPC1, TRPC3-7, and TRPM4-5 were tested using the membrane potential dye. Both dye solutions were made up in HEPES buffered Hank's balanced salt solution (HBSS). Dye solution (90 μL) was added to the wells and incubated at 37° C. for 1 hour. Test compounds and standard inhibitors (10 μL) were then added to the wells and incubated at room temperature for 10 minutes. The plates were then placed in the flexstation and fluorescence monitored every 1.52 seconds. After 20 seconds agonist was added and the fluorescence monitored for 2 minutes at 485 nm/525 nm and 530 nm/565 nm, Ex/Em, for the calcium 5 dye and the membrane potential dye respectively. Controls—TRPV1: capsazepine; TRPV2: tranilast; TRPV3: ruthenium red; TRPV4: ruthenium red; TRPV5: $Gd^{3+}$; TRPA1, ruthenium red; TRPC1: $Gd^{3+}$; TRPC3: Pyr3; TRPC4: ML 204; TRPC5: ML 204; TRPC6: ML 204; TRPC7: SKF 96365; TRPM2: 2-APB; TRPM3: Mef acid; TRPM4: clotrimazole; TRPM5: TPPO; TRPM8: 2-APB. Control data was in all cases within historical range.

Patch-Clamp Assays

The assays were performed at SB Discovery (Glasgow, UK) on a fee-for-service basis. Concentration-response curves and washout assays were performed using a manual patch clamp method. HEK-293 cells were grown and prepared, according to the adapted procedure for hTRPV2 stable cell lines at SB Discovery. Cells were serum starved for approximately 24 hours and then changed to serum-containing media prior to electrophysiology testing. The manual patch-clamp assay was carried out at room temperature using a traditional electrophysiological unit. Cells were used within 2-3 hours after addition of serum containing media to the cells. The standard extracellular solution contained 145 mM NaCl, 4 mM KCl, 2 mM $CaCl_2$, 1 mM $MgCl_2$, 10 mM HEPES and 10 mM glucose. The pH was adjusted to 7.4 with NaOH, and the osmolarity was measured as 311 mOsm/L. The standard intracellular solution contained 50 mM KCl, 10 mM NaCl, 60 mM KF, 2 mM $MgCl_2$, 20 mM EGTA and 10 mM HEPES. The pH was adjusted to 7.2 with KOH and the osmolarity was measured as 286 mOsm/L. A standard ramp protocol was used to monitor currents upon addition of control (extracellular solution) and compound solutions. The voltage protocol consisted of a series of voltage ramps from −100 mV to +100 mV, every 5 seconds, from a holding potential of −60 mV. The maximum outward current values during the recordings at +100 mV were used for analysis. Manual patch clamp experiments were carried out using an Axon 200B amplifier and a Digidata 1440A acquisition system from Axon Instruments (Molecular Devices, USA). The software program pClamp (version 10) from Axon Instruments was used to stimulate and record electrical activity. Capacitative transients were compensated electronically from the recordings, however the voltage drop across the series resistance and the liquid junction potential were not compensated. The series resistance was generally less than 10 MΩ, with a mean cell capacity of approximately 25 pF. The GraphPad Prism (version 5) software was used to analyze and plot all graphs. The agonist (cannabidiol; Abcam #ab120448) was prepared as 100 mM stock in 100% DMSO and diluted to 4 μM or 10 μM in physiological solution prior to testing. Piperlongumine was prepared as 100 mM stock in 100% DMSO and diluted to the specified concentrations in physiological solution (100, 50, 10, 1 and 0.1 μM), also containing 4 μM or 10 μM cannabidiol. Ruthenium red (Sigma, #R2751) was prepared daily as 10 mM stock ion distilled water and diluted to 100 μM in physiological solution.

Intracellular Calcium Imaging

Cells (ATCC) were grown to 50% confluency in DMEM (Gibco) supplemented with 10% FBS (Gibco), GlutaMax (Gibco), MEM and NEAA (Gibco), 4.5 g/L glucose and 0.11 g/L sodium pyruvate. Cells were seeded in μ-ibidi 8 well plates and transfected with TRPV2-RFP[34] (kindly gifted by Prof. Itaru Kojima, Gunma University, Japan). After 48 h of incubation, cells were subjected to calcium imaging. Intracellular calcium measurements were performed with Fura-2 AM (Life Technologies) and modified from previously described studies.[12] In short, 1 hour before the measurement, cells were loaded with 5 μM Fura-2-AM for 45 minutes. Cell medium was replaced by Tyrod's solution (119 mM NaCl, 5 mM KCl, 2 mM $CaCl_2$, 2 mM $MgCl_2$, 6 g/L glucose, 25 mM HEPES pH 7.4). Simultaneously, the respective treatment was added to the cells (final concentration of 1% DMSO (control), 5 μM piperlongumine and 10 μM tranilast) and cells were allowed to re-adjustment for 15 minutes. Fura-2 AM emissions from 340 nm and 380 nm excitation were recorded for 1 minute before TRPV2 was activated by addition of 4 μM or 20 μM cannabidiol (CBD). Image analysis was done using the MetaFluor Analyst software. The statistical analysis was performed with astatsa.com. After calcium imaging acquisition, the cells were immediately fixed with 4% paraformaldehyde for 15 min. Cells were washed trice with PBS and embedded in Fluoromount G. Samples were imaged using the LSM Zeiss 880 microscope.

Immunoblotting

HEK293 cells were transfected with TRPV2-RFP and co-transfected with either negative control siRNA (5 nM) or TRPV2 siRNA (5 nM) and incubated for 48 h. Cells were washed with PBS and lysed in lysis buffer (20 mM HEPES pH 7.4, 150 mM NaCl, 1% Triton-X100, 1 mM EDTA, 0.5% sodium desoxycholate, and protease inhibitor cocktail (Roche)), passed 10 times through a syringe with 25 g needle, incubated on ice for 30 min and centrifuged at 18.000 g and 4° C. for 20 min. The supernatant was precipitated with 3 volumes of acetone at −20° C. overnight. The precipitated protein pellet was re-suspended in an appropriate volume of lysis buffer, combined with 5× reducing SDS sample buffer and boiled for 10 min. Proteins were separated using Tris-Glycine buffered SDS PAGE and transferred to PVDF membrane for 90 min at constant 350 mA.

Membranes were blocked with 10% milk powder in Tris-buffered saline with 0.1% Tween20 for 1 h and immunodetection was performed with antibodies for TRPV2 (Atlas antibodies) and Tubulin (Thermofisher).

Dynamic Light Scattering

Dynamic light scattering (Zetasizer Nano S, Malvern, UK) was used to determine compound colloidal aggregation. The particle sizes were measured at 25° C. Water solubility was measured as described elsewhere with successive measurements within 60 minutes.[35] A 100 mM stock solution of piperlongumine was prepared in DMSO, following dilution to deionized water to obtain an analyte solution of 100 μM (0.1% DMSO). Colloidal aggregation was measured through sequential dilutions.

NCI-60 Screen of Piperlongumine Activity

Piperlongumine was submitted to the NCI-60 Human Tumor Cell Lines Screen and its activity was measured at five concentration levels (0.01, 0.1, 1, 10 and 100 μM) in 59 NCI-60 cell lines with four dose response parameters ($GI_{50}$, $IC_{50}$, $LC_{50}$ and TGI). The TRPV2 normalized gene expression (averaged probe intensities combined from five microarray platforms) in NCI-60 cell lines was downloaded from the CellMiner database[36,37]. The Spearman correlation was used to test the interdependence between TRPV2 expression levels and piperlongumine $IC_{50}$ values against 57 cancer cell lines.

CTRP Screen of Piperlongumine Activity

The TRPV2 robust multi-array average (RMA)-normalized expression and piperlongumine sensitivity data for 775 human cancer cell lines from the Cancer Therapeutics Response Portal (CTRP) v2 were retrieved[23]. The Area Under the dose-response Curve (AUC) was used as the metric of cell line sensitivity to piperlongumine, measured over a 16-point concentration range. Lower AUC values mean higher drug activity. The Spearman correlation was used to test the interdependence between TRPV2 expression levels and piperlongumine's AUC.

Analysis of TRPV2 Prognostic Value in Human Cancer Cohorts

The normalized TRPV2 gene expression (quantified through RNA-seq by Expectation Maximization—RSEM)[38], and clinical data for 9,785 tumour samples belonging to 30 cohorts from The Cancer Genome Atlas (TCGA) were downloaded from Firebrowse. Using the TRPV2 median expression to divide the patients into two subgroups, the prognostic significance was estimated using Kaplan-Meier plots and log-rank tests, per cancer type, through the R package survival[39].

GTEx-TCGA Comparison

The comparison of TRPV2 gene expression between brain tumors from TCGA (507 low-grade glioma (LGG) and 153 glioblastoma multiforme (GBM) samples) and normal brain tissues from Genotype-Tissue Expression (GTEx) project (1,141 samples) was done using TPM (Transcripts Per Million) values calculated by Toil[40].

TCGA Tumor Purity Analyses

Correlation analyses between TRPV2 gene expression ($log_2$ of RSEM) and tumor purity across LGG and GBM samples were performed using TIMER (Tumor IMmune Estimation Resource)[41].

TRPV2 Expression in Brain Single-Cells

The normalized TRPV2 gene expression ($log_2$ of Counts Per Million) in 3,589 single-cells derived from 4 human GBM samples was retrieved from a public database[26]. The normalized TRPV2 expression (Fragments Per Kilobase Million—FPKM) in different purified cell types from adult human brain healthy tissues was retrieved from (Gene Expression Omnibus dataset accession GSE73721)[42].

Toxicity Assays 5,000 cells/well were seeded in 96 well plates with DMEM containing 2% FBS. The next day piperlongumine was added at various concentrations. The total DMSO concentration in each well did not exceed 1%. At 24, 48 and 72 hours the media was removed and replaced with CellTiter-Blue (Promega, 1:20 in media). The plate was incubated for 90 minutes before measuring fluorescence intensity.

Immunohistochemistry Staining

Paraffin embedded samples were sectioned and antigen retrieval was performed (Dako PT link, pH 6, 95° C., 20 minutes). After blocking with 3% $H_2O_2$ in MeOH for 30 minutes, sections were incubated with anti-TRPV2 (Atlas antibodies HPA044993, 1:300) for 1 hour at room temperature, followed by a HRP conjugated secondary antibody (Dako envision anti-rabbit ready to use) for 30 minutes at room temperature. Sections were developed with DAB chromogen (3,3'-diaminobenzidine, Dako) and counter stained with Harris Haematoxylin. Slides were digitalized using NanoZoomer SQ (Hamamatsu).

Over-Expression in HEK293 and U251

75,000 HEK293 cells were seeded in each well of a 24 well plate. The next day cells were transfected with hTRPV2-RFP plasmid (kindly gifted by Prof. Itaru Kojima, Gunma University, Japan). After incubating for 24 hours the media was changed and PL was added at 5 and 10 μM. 24 hours later cell viability was assessed using CellTitre-Blue (Promega) or Annexin V, 7-AAD staining. Transfection efficiency was assessed using flow cytometry.

50,000 U251 cells were seeded in each well of a 24 well plate. The next day cells were transfected with hTRPV2-RFP plasmid. After incubating for 48 hours the media was changed and PL was added at 5 and 10 μM. 24 hours later cell viability was assessed using CellTitre-Blue (Promega). Transfection efficiency was assessed using flow cytometry.

Flow Cytometry

Cells were harvested and fixed with methanol for 10 minutes at −20° C. before being washed with PBS (0.05% Tween 20). Samples were incubated with anti-TRPV2 (Atlas Antibodies, 1:100 in PBS) for 20 minutes followed by goat anti-rabbit Alexa 488 (Abcam, ab150077, 1:500 in PBS) secondary antibody. BD LSRFortessa X-20 with FACS Diva software was used for analysis.

Annexin V, 7-AAD Viability Assay

Cells were harvested from plates by washing with media (HEK293) or TrypLE express (Gibco). The media was removed after centrifugation and the cells were washed twice with binding buffer before being incubated for 30 minutes at room temperature with Annexin V-APC (eBiosciences, 1:100) and 7-AAD (Pharmigen, 1:50). Samples were diluted with binding buffer and analyzed by flow cytometry using BD LSRFortessa X-20 with FACS Diva software. Samples with single stains were used as controls.

Piperlongumine Encapsulation into β-Cyclodextrin

Piperlongumine (abcr GmbH) in ethanol was incubated with 2-hydroxypropyl-β-cyclodextrin (Carbosynth Ltd) in water at a ratio of 1:2 and stirred for 1 hour at room temperature. The solution was then evaporated to dryness.

Piperlongumine Hydrogel Scaffold Synthesis and In Vivo Intracranial Implantation.

Hydrogel scaffolds were developed as previously described[27-30]. Briefly, equal parts of dendrimer amine of 12.5% solid content and dextran aldehyde 5% solid content were mixed to form pre-cured disks. For doped scaffolds, 50 mg/kg of piperlongumine previously encapsulated with β-cyclodextrin were added to the dextran solution prior to hydrogel formation. Pre-cured disks were formed and implanted intra-cranially into the right cerebral hemisphere of mice-bearing GBM tumors or used for in vitro assays.

Piperlongumine Release from Hydrogel Scaffold In Vitro

Pre-cured disks of hydrogel scaffold alone or doped with piperlongumine previously encapsulated with β-cyclodextrin were incubated in PBS at 37° C. At different time points samples were collected from the PBS and the released piperlongumine was quantified using liquid chromatography—mass spectrometry, by integrating the area under the peak corresponding to piperlongumine. Data were plotted as the percentage of total piperlongumine encapsulate in the hydrogel for each time point.

Cell Viability Tests with Piperlongumine Doped Hydrogel.

24 well plates were seeded with 50,000 U251 cells per well. After 24 hours transwell permeable support inserts (6.5 mm insert, 8.0 µm PET membrane, Costar) containing pre-cured disks of hydrogel scaffold alone or doped with piperlongumine previously encapsulated with β-cyclodextrin were added to the wells. After 24, 48 and 72 hours cell viability was measured using CellTiter-Blue reagent (Promega, 1:20 in media).

Preparation of U251-GFP-Luciferase Cell Line.

50,000 cells per well were seeded in 6 well plates. The following day 3 mL of lentivirus-GFP-luciferase (produced by Carlos Custodia November 2016) and 4 µL of polybrene was added to a well. The virus containing media was removed after 48 hours and replaced with fresh DMEM with 10% FBS. Cells were expanded and sorted using FACS. Vials of confluent cells were frozen until required for in vivo experiments.

Piperlongumine Doped Hydrogel as a Treatment for GBM in Xenograft Mouse Model.

All mouse studies were approved by the ethical committee and experiments were performed according to their regulations and policies. Glioblastoma xenografts were established in 8 week-old male athymic nude mice (Charles River Laboratories). Once mice were anaesthetised with isoflurane and immobilised on a stereotactic frame, a burr hole, 2.7 mm in diameter, was made 2.5 mm lateral and 1.5 mm posterior to bregma, above the right cerebrum. 250,000 glioblastoma cells (U251-GFP-luc) in a volume of 3 µL PBS were injected into the brain at a depth of 2.5 mm (needle lowered 3 mm then retracted 0.5 mm to create a pocket for the cells) using a blunt ended needle and Hamilton syringe. The needle was kept in place for 5 minutes to minimize cell reflux. Once the needle was removed the incision was sutured and the animals were allowed to recover. Eight days after tumor induction the mice were imaged using the IVIS Lumina system. The mice were ranked according to their bioluminescent signal and divided into 2 equal groups. Nine days after tumor induction the mice were anaesthetised via intraperitoneal injection of medetomidine and ketamine and the sutures were re-opened. The hole in the skull was located and the tissue on the surface was disrupted before applying the hydrogel (pre-cured disks of hydrogel scaffold alone for the control group or doped with piperlongumine (50 mg/kg) previously encapsulated with (β-cyclodextrin) to ensure that the hydrogel was in contact with brain tissue. The skin was re-sutured and the anaesthesia was reversed with antipamezole. Assessment of in vivo toxicity via mice body weight evaluation was performed on all the animal groups during the experiment. Three weeks after hydrogel implantation the mice were sacrificed to ensure tumor size did not surpass humane endpoints. Organs including the brain and spinal cord were harvested for histological evaluation. Histological sections of the tumors (n=5) were stained with hematoxylin and eosin and for immunohistochemical analysis the tumors (n=5) were stained with the antibodies anti-TRPV2 (Atlas antibodies, HPA044993, dilution 1:200) and anti-Ki67 (Abeam ab15580, dilution 1:200). The survival curve was plotted based on a cut off value of 554% increase in the original tumor size measured by IVIS lumina 8 days after tumor induction. This value was set as in previous experiments the tumors were able to grow to such a volume that the skull became distorted. This was only visible after histological sections of the head were analyzed and it was decided to set a value in order to ensure the endpoint was humane and clinically relevant.

Analysis of Tumour Growth.

Non-invasive longitudinal monitoring of tumor progression was followed by scanning mice with the IVIS Lumina-bioluminescent and fluorescent imaging system (Xenogen IVIS Lumina, Perkin Elmer). Fifteen minutes before imaging, mice were subcutaneously injected with 150 µL of D-luciferin (30 mg/mL, Perkin Elmer) in PBS (Lonza). Whole-animal imaging was performed at the indicated time points (−1, 3, 6, 10, 13, 18 and 21 days post intracranial implantation of hydrogel disks).

Real Time Quantitative RT-PCR (QPCR)

Total RNA was isolated using the TRIzol™ Reagent according to the manufacturer's protocol (Sigma, Darmstadt, Germany). 500 ng RNA was converted to cDNA using Superscript III (Promega, Mannheim, Germany) and 25 ng cDNA as template for quantitative PCR with GoTaq qPCR Master Mix (Promega, Mannheim, Germany). Quantitative PCR was performed for TRPV2 with a StepOneplus detection system (Applied Biosystems, Foster City, USA). Thermal cycler conditions were 95° C. for 20 min, then 40 cycles of 3 min at 95° C., followed by 30 sec at 60° C. mRNA expression was calculated using the 2-ΔCT method and normalized to the internal control PGK1.

Sample Preparation

Proteins were extracted from frozen tissue sections as described elsewhere (Poschmann et al. [1]). Briefly, cells were homogenised in urea buffer with a TissueLyser (Qiagen, Hilden, Germany) and subsequent sonication. After centrifugation for 15 min at 14,000×g and 4° C., supernatants were collected and proteins contained were precipitated overnight at −20° C. with acetone at a 1:4 (v/v) ratio. Protein concentration was determined via Pierce 660 nm Protein Assay (Fischer Scientific, Schwerte, Germany) and 10 µg protein per sample were desalted through electrophoretic migration at 50 V for 10 min on a 4 -12% Bis-Tris polyacrylamide gel (Novex NuPAGE, Thermo Scientific, Darmstadt, Germany). After silver staining, protein bands were cut out reduced, alkylated and digested with trypsin before peptide extraction via sonication. Peptides were dissolved in 16 µL 0.1% TFA (v/v) and the peptide concentration was measured under application of an o-phthaldialdehyde assay.

LC-MS Analysis

For mass spectrometric analysis, 15 µL peptide solution per sample were analysed on a nano-high-performance liquid chromatography electrospray ionisation mass spectrometer. The analytical system was composed of a RSLCnano U3000 HPLC coupled to a QExactive plus mass spectrometer via a nano-electrospray ion source (Thermo Fischer Scientific, Bremen, Germany). Injected peptides were concentrated and desalted at a flow rate of 6 µL/min on a trapping column (Acclaim PepMao $C_{18}$, 2 cm×100 µm×3 µm particle size, 100 Å pore size, Thermo Fischer Scientific, Bremen, Germany) with 0.1% TFA (v/v) for 10 min. Subsequently, peptides were separated at a constant flowrate of 300 nL/min over a 120 min gradient on an analytical column (Acclaim PepMap RSLC $C_{18}$, 25 cm×75 µm×2 µm particle size, 100 Å pore size, Thermo Fischer Scientific, Bremen, Germany) at 60° C. Separation was achieved through a gradient from 4 to 40% solvent B (solvent A: 0.1% (v/v) formic acid in water, solvent B: 0.1% (v/v) formic acid, 84% (v/v) acetonitrile in water). Afterwards, peptides were ionised at a voltage of 1,400 V and introduced into the mass spectrometer operated in positive mode. MS scans were recorded in profile mode in a range from 350-2000 m/z at a resolution of 70,000 while tandem mass spectra were recorded at a resolution of 17,500. Tandem mass spectra were recorded with a data dependent Top10 method and 30% normalised collision energy. Dynamic exclusion was activated with a repeat count of 1 for 100 ms.

Computational Mass Spectrometric Data Analysis

Proteome Discoverer (version 2.1.0.81, Thermo Fisher Scientific, Bremen, Germany) was applied for peptide/protein identification with Mascot (version 2.4.1, Matrix Science, London, UK) as search engine employing the UniProt database (human; including isoforms; date 2018-05-01). A false discovery rate of 1% ($p \leq 0.01$) on peptide level was set as identification threshold. Proteins were quantified with Progenesis QI for Proteomics (Version 2.0, Nonlinear Dynamics, Waters Corporation, Newcastle upon Tyne, UK).

Pathway Analysis

Gene sets were comprised of curated pathways from several databases including GO, Reactome, KEGG (Mar. 24 2016 and visualized using Cytoscape (www.cytoscape.org; $p \leq 0.001$, $q \leq 0.05$, similarity cutoff 0.5). Mass spectrometry data was analysed in primary and recurrent pairs and the T value was used to perform a ranked analysis. Ingenuitiy pathway analysis (IPA) used the sigfnificant genes form the paired T-test ($p \leq 0.05$ and fold change±2). Significance of IPA was determined based on $p \leq 0.05$. Heatmaps and hierarchical clustering were performed by normalizing mean expression to 0 with a standard deviation of 1 and using Pearson's dissimilarity algorithm and average linkage in Partek Genomic Suite (Partek Incorporated, Missouri, USA).

Figure 1A:
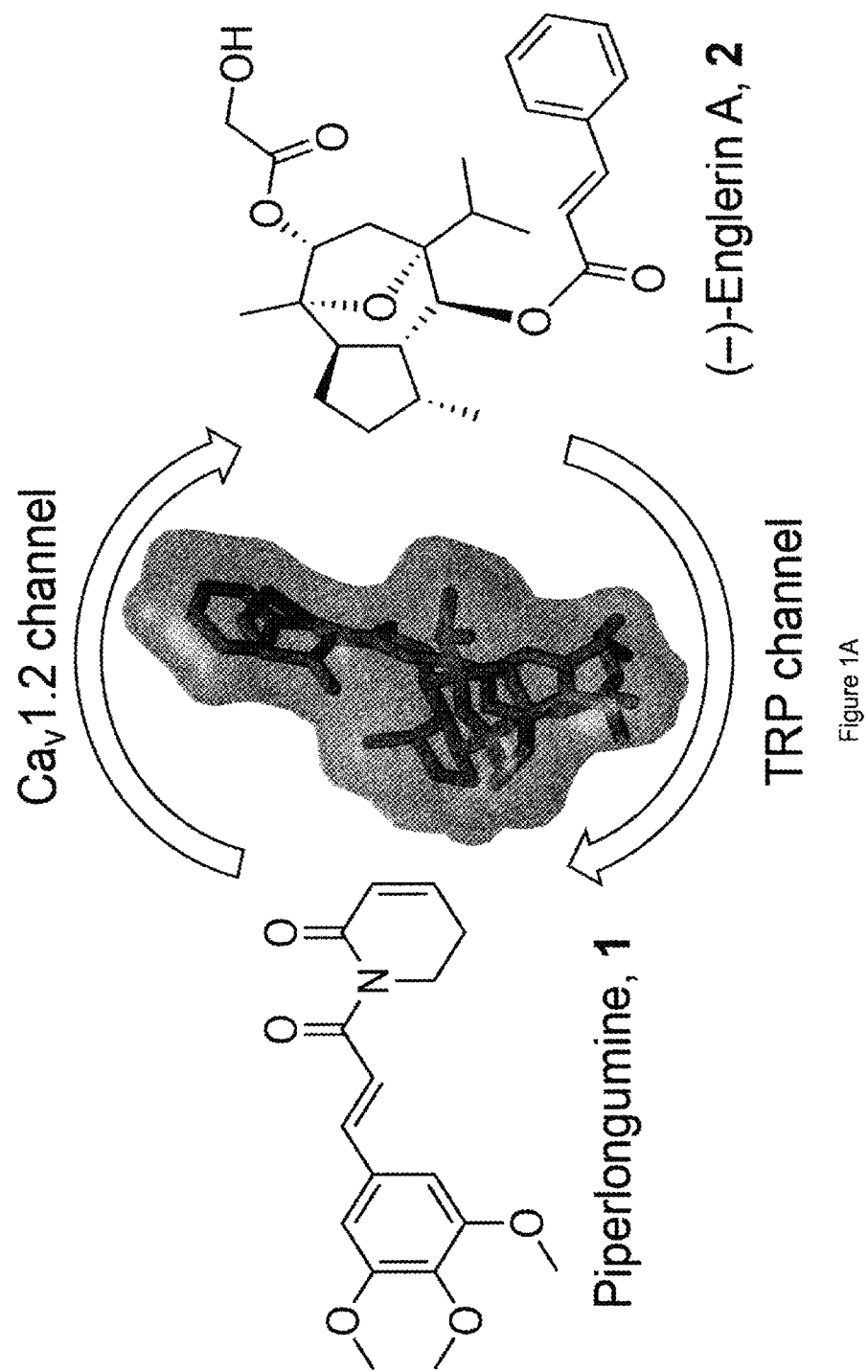
FIG. 1A shows the structures of piperlongumine, 1, and (−)-englerin A, 2, and the mutual target engagement relationship.
Figure 1B:
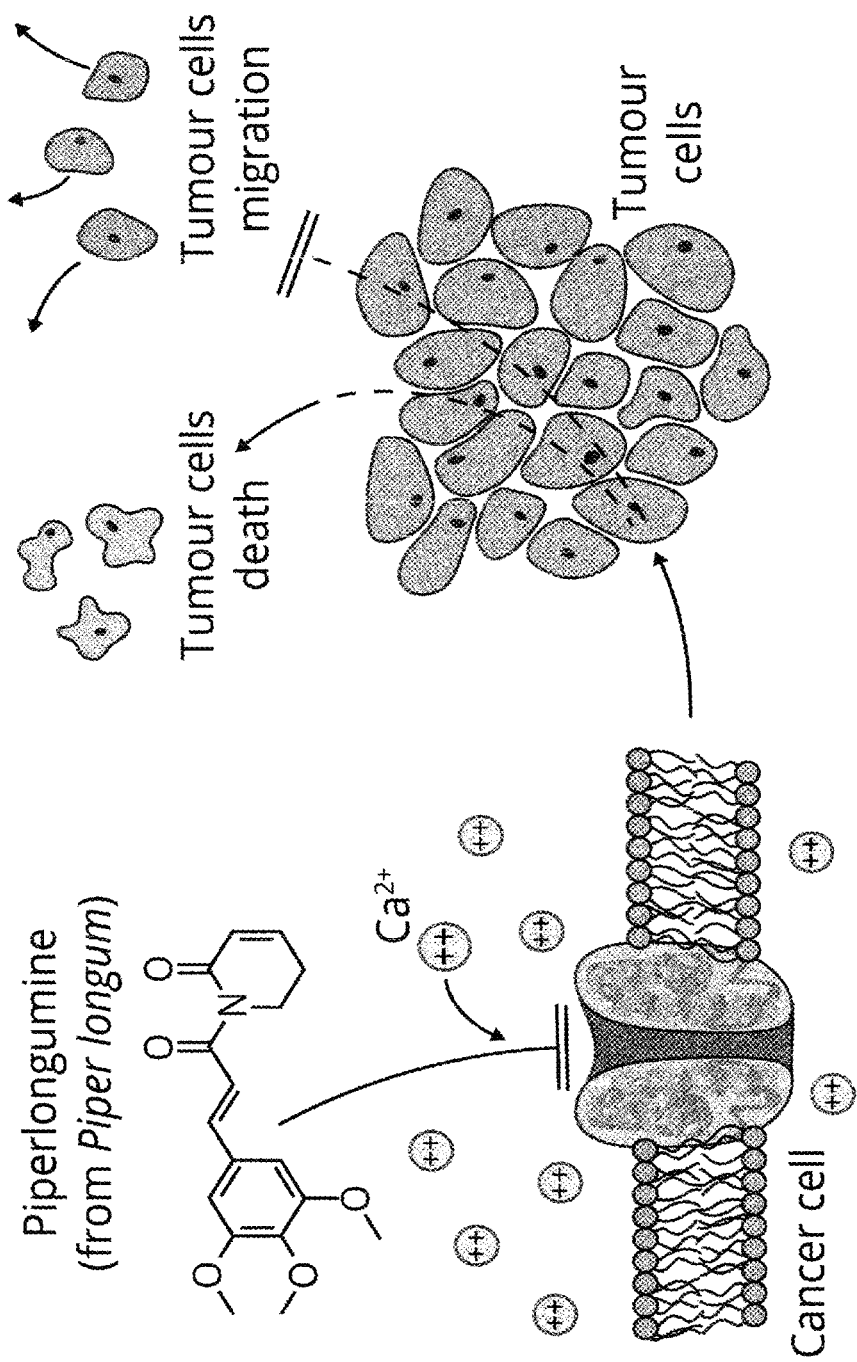
FIG. 1B is a schematic of the effect of piperlongumine on cancer cells.
Figure 2:
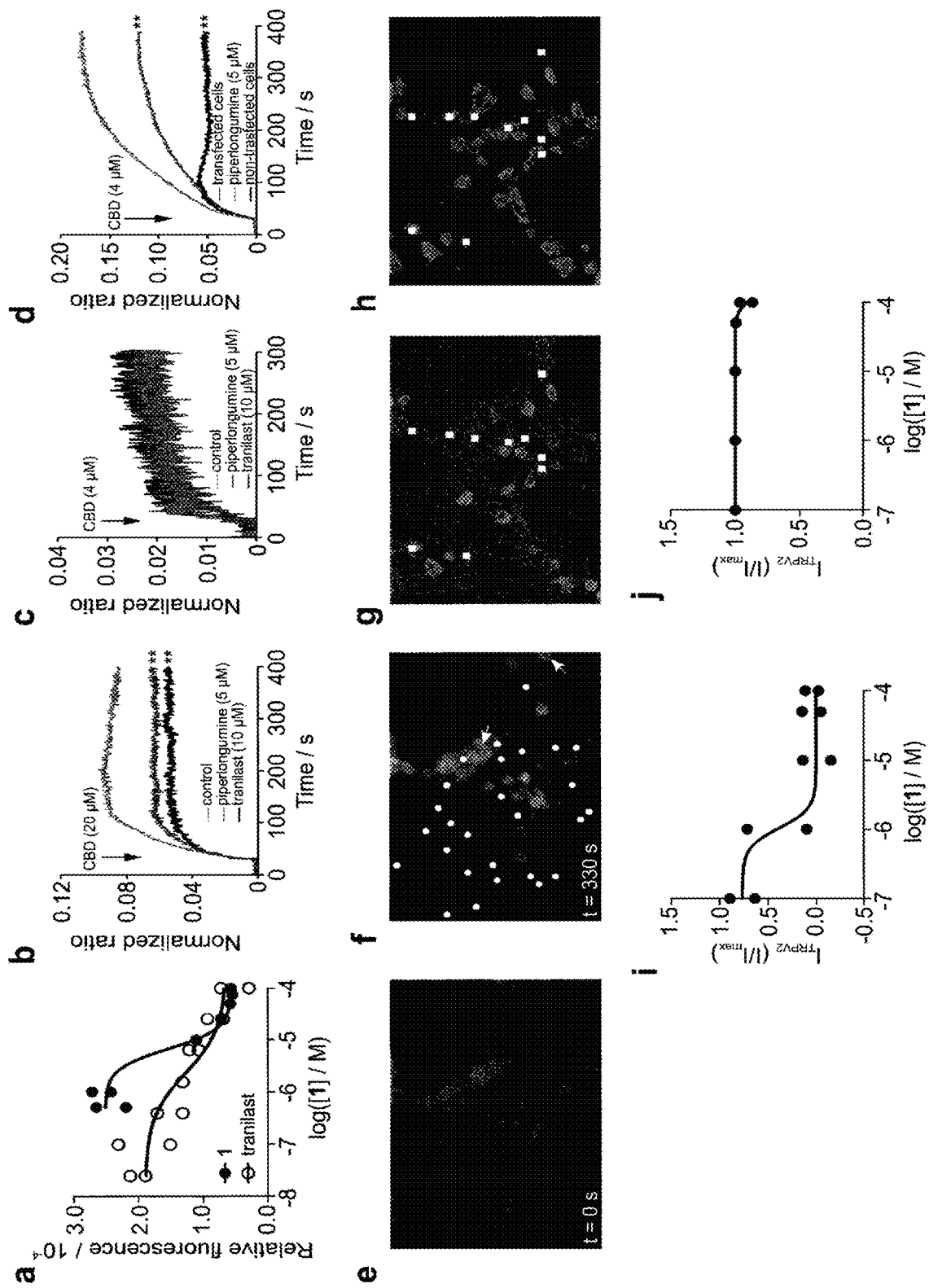
FIG. 2 shows that piperlongumine, 1, modulates TRPV2. a) Concentration-response curve of 1 against TRPV2, using a fluorescence-based assay. $IC_{50}$=4.6±0.13 log units, n=2; control: tranilast, $IC_{50}$=2.3±0.25 log units, n=2. b) Inhibition of cannabidiol (CBD, 20 μM) evoked calcium influx by 1 (5 μM) in HepG2 cells (0.5% DMSO). For quantification, the five strongest responding cells were analyzed in each well (n=35-45 cells) and normalized to the baseline. The average of the five strongest responding cells are depicted. One-way ANOVA and Tukey HSD post hoc test: significant difference between control and 1 (p<0.01) and between control and tranilast (p<0.01) at 120 s post stimulation. No significant difference between 1 and tranilast. c) Inhibition of CBD (4 μM) evoked calcium influx by 1 (5 μM) in HepG2 cells (0.5% DMSO). No statistically significant difference is observed between all samples. d) Inhibition of CBD (4 μM) evoked calcium influx by 1 (5 μM) in HEK293 cells (0.5% DMSO). Negative control: non-transfected HEK293 stimulated with CBD (4 μM). For quantification the ten strongest responders/well were analyzed and normalized to the baseline (transfected cells: n=70-80, non-transfected cells: n=20). The average of the ten strongest responding cells are depicted. One-way ANOVA and Tukey HSD post hoc test: significant difference between control and 1 (p<0.001), between control and non-transfected HEK293 cells (p<0.001) and between non-transfected HEK293 cells and 1 (p<0.001) at 300 s post stimulation. e) Calcium imaging of HEK293 transfected with the human TRPV2-RFP fusion protein, corrected for baseline level. f) Calcium level after 5 min of 4 μM CBD stimulus (color code—blue=low calcium level; green=intermediate; yellow=medium high; red=high). Non-transfected cells are marked by dots. Cells showing artefacts (e.g. calcium oscillation) are marked with an arrow. None of the non-transfected cells show strong calcium influx. g) The ten strongest responding cells, marked with squares, express TRPV2-RFP at moderate levels. h) Artificially enhanced RFP signal: all of the ten selected cells express TRPV2-RFP. i) Concentration-response curve of 1 against TRPV2, using a patch-clamp assay. $IC_{50}$=1 μM±0.52 log units, n=2, stimulus: 4 μM CBD. j) Concentration-response curve of 1 against TRPV2, using a patch-clamp assay. $IC_{50}$>100 μM, n=2, stimulus: 10 μM CBD.

We hypothesized that the pharmacophore relationship between 1 and 2 (FIG. 1A) encompasses the blueprints for TRP modulation, a hitherto unknown drug target family for 1 that may partly explain its potent anticancer and/or antimetastatic activities. We further motivated testing of 1 against TRP channels through a confident binding prediction by means of machine learning. The unique architecture of the ligand-based algorithm we used has been shown effective in recognizing ligand-target relationships for NPs that are overlooked by competing tools.[2] With a binding hypothesis in hand, we engaged in a screening effort against a panel of human, ligand-gated TRP channels, including the vanilloid (TRPV), canonical (TRPC), melastatin (TRPM) and ankyrin (TRPA) counterparts, using a cell-based expression system coupled with a fluorescent calcium detection probe. Remarkably, 1 did not activate any of the assayed channels and only potently inhibited dose-dependently the cannabidiol-evoked calcium influx via TRPV2 ($IC_{50}$=4.6 µM±0.13 log units, Ligand Efficiency=0.32; Table 1 and FIG. 2a). We performed calcium-imaging experiments using the Fura2-AM calcium probe in HepG2 cells, which we confirmed to express TRPV2 (FIG. 2b,c). The calcium influx evoked by 20 µM cannabidiol could be significantly inhibited upon cell treatment with 5 µM of 1 (p<0.01, one-way ANOVA and Tukey post hoc test), in similar fashion to the control compound tranilast at a concentration of 10 µM (FIG. 2b). Interestingly, stimulation with 4 µM of cannabidiol did not elicit intracellular calcium increase (FIG. 2c), suggesting a low copy number of TRPV2 channels in HepG2, and limitations of its use as a model system.

We then transfected HEK293 cells with the required plasmid DNA to allow for transient over-expression of the TRPV2-RFP fusion protein (FIG. 2d-h). The transfected cells were subsequently stimulated with 4 µM of cannabidiol and treated with 1 to corroborate the functional effects previously observed (FIG. 2d). Besides activating TRPV2, cannabidiol modulates the CB1 G-protein coupled receptor, and displays intricate polypharmacology at micromolar concentrations.[19] To rule out calcium influx due to modulation of targets other than TRPV2 we also stimulated non-transfected HEK293 with cannabidiol. Indeed, despite modulation of other targets, the bulk of calcium influx in transfected HEK293 cells arises from engagement of TRPV2 channels.

Our data further shows that inhibition of calcium influx by 1 in transfected HEK293 cells is significantly different from the calcium influx in non-transfected control cells (p<0.001, one-way ANOVA and Tukey HSD post hoc test). Thus, the effects displayed by 1 are ascribed to TRPV2 modulation.

Using patch-clamp as an orthogonal technology we confirmed binding to the TRPV2 channel and functional antagonism via interruption of calcium currents evoked by 4 µM of cannabidiol ($IC_{50}$=1 µM±0.52 log units, FIG. 2i). Importantly, the inhibitory effect by 1 is abrogated upon prior stimulation of TRPV2 with 10 µM of cannabidiol ($IC_{50}$ (1)>100 µM, n=2; $EC_{50}$ (cannabidiol)=3.8 µM, nHill=0.6, n=3; FIG. 2j). Our data thus suggests specific and directed molecular recognition by 1 and the absence of artefactual inhibition of TRPV2. Dynamic light scattering data further supports the absence of colloidal aggregate-induced inhibition—a common phenomenon for false positive readouts.

Figure 3:
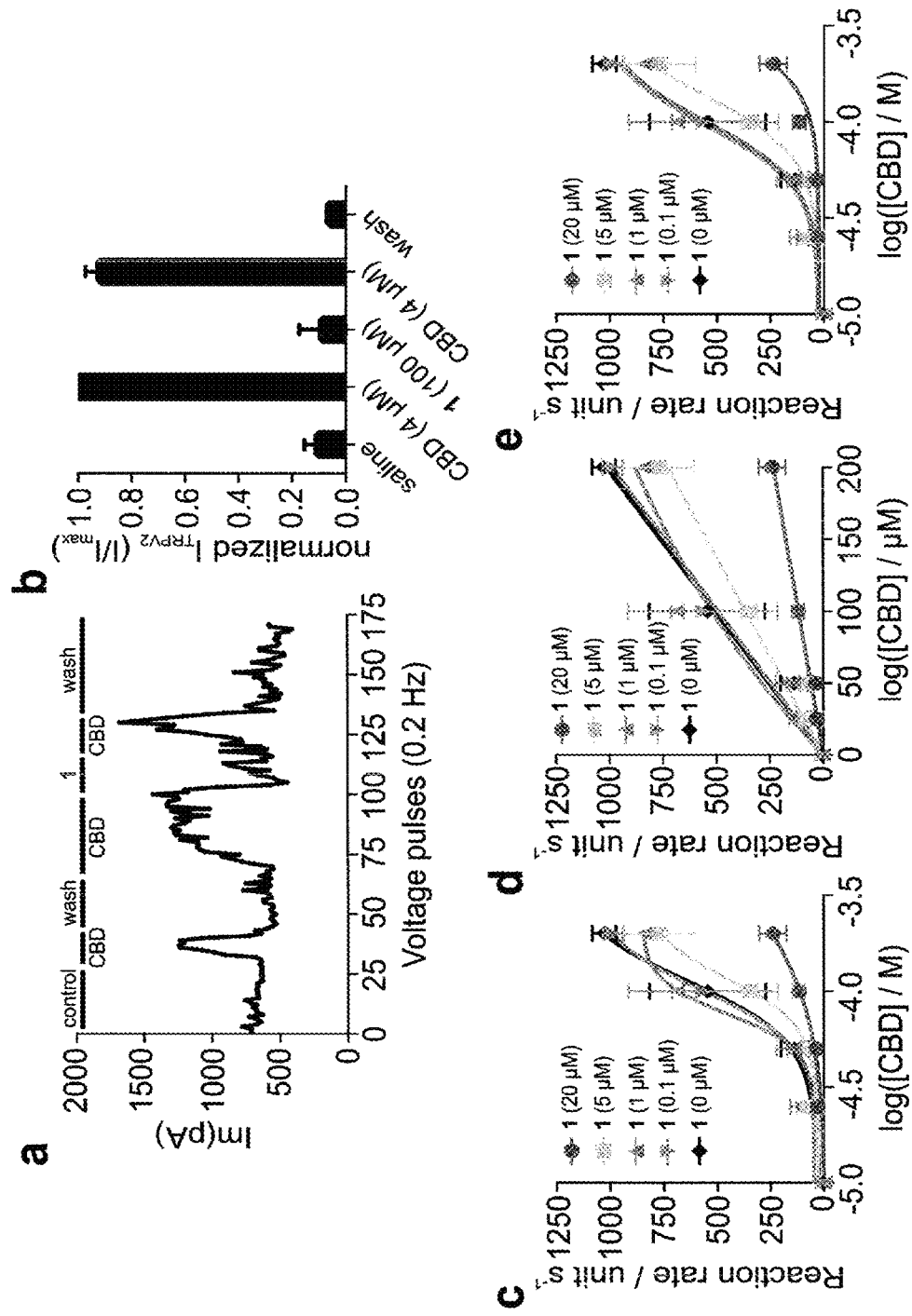
FIG. 3 shows piperlongumine, 1, is a selective human TRPV2 allosteric antagonist. a) Exemplary patch-clamp time-course trace showing inhibitory effect of 1 (100 μM)

The remarkable selectivity revealed by 1 was partly unexpected. While 1 has low substructural similarity to known TRPV ligands (average Tanimoto index=0.10, Morgan fingerprints, radius 2, 2048 bits) it still populates charted TRPV bioactive space, according to the CATS auto-correlation topological pharmacophore descriptor (MOE 2016.10, Chemical Computing Group implementation,). The obtained activity profile is also intriguing and challenges flagging systems for chemical matter prioritization in early discovery programs. Piperlongumine is readily flagged by common substructure-based filters, such as those in the pan assay interference compounds (PAINS),[20] and the rapid elimination of swill (REOS)[21] that identify, among others, Michael acceptors as structural alerts. Incubation of 1 with N- and C-protected cysteine under bioorthogonal conditions yielded stable cysteine adducts, as assessed by mass spectrometry. A similar observation had already been made by Adams et al.[17] It would thus be reasonable to consider a promiscuous target engagement behaviour and general reactivity of 1 with free cysteine residues across the human proteome. To address the possibility of irreversible binding of 1 to TRPV2 we performed a series of incubation and washout experiments (FIG. 3a,b). Gratifyingly, the activity of TRPV2 could be fully restored upon washout, providing robust evidence that binding is either non-covalent or that 1 presents a fast off-rate after covalent modification of TRPV2.

Spurred by the obtained data we next endeavoured to gain insights into the mode of binding of 1 to TRPV2, for which we performed co-incubation experiments with cannabidiol. With increasing concentrations of 1 the maximal effect on $EC_{50}$ curves of cannabidiol decreased, which is typical of non-competitive (allosteric) antagonism (FIG. 3c).[22] Moreover, at concentrations of 1 higher than 5 µM the apparent $v_{max}$ value of cannabidiol is reduced, also in agreement with allosteric inhibition—an increase in agonist concentration cannot surmount the functional effects of 1 (FIG. 3d). Schild plots further support the mode of inhibition given that both curves and Hill slopes are fully consistent with our previous data (FIG. 3e).

Next, we used isothermal titration calorimetry to screen 1 at 100 µM against different constructs of the rabbit, sperm whale and chiru TRPV2 orthologues. Compound 1 did not bind to any of the constructs. Albeit preliminary, the data hints at key features for molecular recognition. We aligned TRPV2 protein sequences of the studied species to identify dissimilarities, and thus potential binding domains for 1. Strikingly, the so-called TRPV2 pore turret region differs considerably between orthologues. Binding to the turret by a naturally occurring peptide has been shown relevant for engagement of TRPV1.[23] Though, no such relationship has been established for ligands of TRPV2, which further prompted us to build a TRPV2 chimera by substituting the native human TRPV2 turret with the rabbit counterpart. Importantly, HEK293 cells transfected with the chimera TRPV2 channel were equally sensitive to cannabidiol at 4 µM in calcium imaging experiments, providing indication that its binding site topology had not been disturbed.

We then investigated if modulation of TRPV2 by 1 correlated with its cytostatic activity. To that end, the putative anti-proliferative activity of 1 was tested against the NCI-60 panel of human cancer cell lines, representing 9 different cancer types (FIG. S3),[24] at five different concentrations. We transformed the anti-proliferative activity parameters $GI_{50}$ and $IC_{50}$ into their –z scores, whereby high values correspond to high sensitivity of cell lines to 1. Overall, blood, colon and skin cancer cell lines were found to be the most sensitive to 1 (FIG. 4a,b).

To probe the role of TRPV2 on the anti-proliferative effects of 1, we sought for correlation between the cytostatic effects evoked by 1 and TRPV2 mRNA expression. Consistent with our in vitro analyses, cell lines expressing TRPV2 were very sensitive to 1, based on both $GI_{50}$ (Spearman correlation coefficient ($\rho$)=0.28, $p<0.05$; FIGS. 4c) and $IC_{50}$ ($\rho$=0.29, $p<0.05$; FIG. 4d) values. To the best of our knowledge, no association between TRPV2 antagonism and inhibition of cancer cell growth had been previously made. However, the sensitivity to 1 of cell lines not expressing TRPV2 suggests modulation of additional targets. Interestingly, no significant correlation was observed for other known targets of 1, i.e. STAT3[18,25] and NF-kB[26]. Still, our analysis on the mRNA expression level does not capture the high dependency of these proteins' activity on other levels of regulation, e.g. STAT3 phosphorylation or NF-kB inhibitor degradation. Subsequently, we expanded the analysis towards all mRNA expression data publicly available for the NCI-60 panel. Genes ranked according to the Spearman correlation coefficient between their expression and $GI_{50}$ of 1 were used to run Gene Set Enrichment Analysis (GSEA),[27,28] allowing us to identify pathways (false discovery rate<5%) suggesting potential target (gene sets with positive Normalized Enrichment Score (NES), FIG. 4e) and drug resistance (negative NES, FIG. 4e) mechanisms. RNA processing—e.g. spliceosome, ribosome, RNA degradation, RNA polymerase—are among the positively associated pathways (FIG. 4e), likely due to their higher activation in fast dividing cells, where 1 activity is higher. Genes in the positively enriched antigen processing and presentation pathway do not overlap with targets of NF-kB, a central mediator of the human immune response,[29] suggesting that 1 could be affecting different mechanisms of immunity.

Intrigued by the high expression of TRPV2 mRNA in blood and skin cancers in the NCI-60 panel, we explored the use of TRPV2 as a prognostic marker and potential drug target. By analyzing RNA-seq data from the Genotype-Tissue Expression project,[30,31] we confirmed higher expression of TRPV2 in blood but not in normal skin tissue. We further investigated TRPV2 expression across The Cancer Genome Atlas (TCGA, https://cancergenome.nih.gov/) tumour samples. Indeed, TRPV2 is highly expressed in human haematological and skin cancers, but the lack of expression data for normal tissue in both the respective TCGA cohorts does not allow for testing TRPV2 overexpression in those cancer types. Interestingly, lung exhibits the highest expression of TRPV2 amongst normal tissues, contrasting with the very low expression levels in TCGA lung tumour samples, as also observed in NCI-60 cancer cell lines. Accordingly, survival analyses revealed a prognostic value for TRPV2 only in lung cancer types, in four different cohorts ($p<0.05$).[32-35] Lower expression is associated with poorer patient survival.

Altogether these results highlight TRPV2 as a potential prognostic marker in lung cancer. Keeping in mind the caveats of gene expression analysis, e.g. mRNA levels may not be fully translated into protein content, our data remains indicative and should be interpreted with healthy scepticism. Considering that TRPV2 has been shown overexpressed on a protein level, in cancer cell lines and stages other than those sampled in the NCI-60 panel,[36] it is feasible that 1 induces phenotype changes via TRPV2 modulation other examples.

TRPV2 has been decisively implicated in metastatic breast and prostate cancers as a mediator of cell migration.[36-39] To probe the importance of the compound 1-TRPV2 interaction on cell migration we first tested the prostate cancer PC3 and LNCaP cell lines for sensitivity to 1. We treated cells with 5 and 10 µM of 1, in line with the previously determined $IC_{50}$ value against TRPV2. In both cases, cell viability was compromised over 24 hours. Instead we set up a 24-hour long wound-healing scratch assay with the TRPV2-expressing HepG2 cell line, where treatment with 5 µM of 1 during the experiment time course did not induce significant cell death. Compound 1 significantly reduced migration of HepG2 cells over time, in similar fashion to the TRPV2 inhibitor control tranilast (FIG. 5a-c). The results were reproducible in another hepatocarcinoma cell line—Huh-7. Moreover, the anti-migration effect displayed by 1 is dependent on the medium calcium concentration, suggesting the disruption of calcium transport as one mechanism of action.[40,41] To further assess the importance of TRPV2 modulation in the context of HepG2 migration we manually collected a panel of 175 macromolecules correlated with migration of cancer cells.[42-46] For example, these included kinases, GPCRs, ion channels, and transcription factors that play key roles in calcium signalling (FIG. 5d). HepG2 RNA-seq data was collected from ENCODE[47] and a mean gene expression was calculated for each of the targets. Our data shows that TRPV2 is overexpressed in comparison to 89% of the analyzed targets. While polypharmacology explains the net effect of 1 on cancer cell migration, inhibition of TRPV2 ranks among the most relevant mechanisms.

hTRPV2 is a Marker of Poor Prognosis in GBM.

To probe the role of hTRPV2 on the anti-proliferative effects of piperlongumine (PL), we sought for a correlation between the cytostatic effects evoked by PL and hTRPV2 mRNA expression. To that end, we screened PL against the NCI-60 panel of cancer cell lines and analyzed the publicly available CTRP data[23]. Gratifyingly, cell lines expressing hTRPV2 were very sensitive to PL in both drug screens, which suggests the importance of hTRPV2 as a drug target in cancer (Spearman's correlation coefficient, $\rho$=0.29 and 0.24, p=0.03 and $1.5 \times 10^{-11}$, for the NCI-60 and CTRP panels, respectively; FIG. 4d).

To further investigate the role of hTRPV2 in cancer, we tested its prognostic value in 30 cohorts from The Cancer Genome Atlas (TCGA). Indeed, high hTRPV2 expression was found to be strongly associated with poor patient survival in brain tumors (p=$4.37 \times 10^{-13}$, log-rank test), including both within the low-grade glioma (LGG)[24] and GBM[25] cohorts individually (p=0.028 and 0.0087, respectively, log-rank test; FIG. 6). In addition, we found a significant increase of hTRPV2 expression concomitant with tumor stage (FIG. 16). Within the LGG and GBM samples, hTRPV2 expression is negatively associated with tumor purity (Spearman's correlation coefficient, p=−0.45 and −0.36, p=$7.5 \times 10^{-25}$ and $3.1 \times 10^{-14}$, respectively; FIG. 17), thus indicating it is mainly expressed in the tumor microenvironment. Next, we analyzed the expression of hTRPV2 in brain tumor tissue samples from a panel of patients presenting GBM grades II-IV. The immunohistochemical analyses revealed that hTRPV2 is indeed expressed in tumor cells (punctate staining) more so than in the tumor margin (FIG. 7). Most significantly, we observed that high-grade GBM over-express hTRPV2 on the surface and in the cytoplasm of epithelial cells within the tumor. Altogether, this links with that fact that high hTRPV2 expression plays a role in angiogenesis and tumor progression and associates with poor prognosis. Indeed, our results parallel findings obtained from bioinformatics analysis of a fully independent dataset[26] (FIG. 8 left panel).

hTRPV2 Over-Expression Leads to Increased PL Toxicity.

Having identified in silico a correlation between hTRPV2 expression and GBM grades we subjected the TRPV2+ glioma U251 cells to transient over-expression of hTRPV2 with the goal of exacerbating signaling pathways involving hTRPV2. The treatment of transfected cells with 5 µM PL showed reduced viability compared to the non-transfected controls (p=0.0002, n=9, Mann-Whitney test), as assessed by CellTiter Blue, Annexin V and 7-AAD staining (FIG. 8 right panel). This data fully corroborates our analyses and confirms that hTRPV2 is not only a cellular target of PL but also that ligand-target engagement results in cell death. Importantly, U251 cells were sensitive to PL in a dose- and time-dependent manner, to which modulation of hTRPV2 may be factored in. An identical result could be achieved with transiently TRPV2-transfected HEK cells.

Piperlongumine Doped Hydrogel as a Novel Local Treatment for GBM

We next explored the therapeutic potential of PL in a xenograft mouse model of GBM. We encapsulated PL in cyclodextrin in a 1:2 ratio, which dramatically improved its aqueous solubility. Furthermore, to enhance the therapeutic efficacy, we created a therapy suitable for post-surgical administration. To this end, we devised implantable hydrogels that were doped with PL encapsulated in β-cyclodextrin. Using this novel material for local and sustained PL delivery into the brain, we obtained a high concentration of PL at the tumor site and minimal leakage to healthy tissues and organs. To enable the PL release to the tumor tissue and avoid material migration and release to adjacent sites, the hydrogel was decorated with aldehyde groups that interact with tissue amines to form adhesive bonds, as previously reported[27-30]. Profiling of our hydrogel material for the PL release rate under physiological conditions (PBS, pH 7.4, at 37° C.) showed a significant discharge release in the first 4 hours followed by a steady release of small amounts of PL (3% of total) for at least 192 hours. This data provides a rationale to the in vitro toxicity experiments in which PL doped hydrogels were able to induce near complete cell death after incubation with U251 cells for just 24 hours. The empty hydrogels did not have any effect on cell viability.

We proceeded to study the in vivo therapeutic efficacy of the PL doped hydrogels in a GBM mouse model. Hydrogel scaffolds loaded with PL were implanted in the supratentorial region of the brains of athymic nude mice (Crl:NU (NCr)-Foxn1$^{nu}$) 8 days after tumor induction with $2.5 \times 10^5$ U251-GFP-luc cells (FIG. 9). For control group, we employed empty hydrogels, i.e. lacking the PL component, as implants. Inhibition of tumor progression was then measured by bioluminescence of the luciferase expressing GBM cell line via a live imaging system, at regular intervals, for 21 days post-hydrogel implantation and 30 days post tumor induction. The PL doped hydrogel resulted in near complete remission as evident by bioluminescence imaging (p=0.0159, n=5, Mann-Whitney test, FIG. 10) 21 days post hydrogel implantation. Indeed, the difference in survival between the two groups was significant (p=0.0494, log-rank (Manel-Cox test; FIG. 11) which may represent a major achievement in GBM therapy. Furthermore, to validate the safety of the constructs, organs were harvested from mice 21 days post hydrogel implantation and stained for pathological analyses. Our data clearly shows that the in vivo application of doped hydrogels did not cause any damage in lung, liver, kidney, spleen, heart, and intestine, when compared to the empty hydrogel control group. Nevertheless, the tumor tissue shows extensive reduction in vascularization, in accordance with tumor size reduction following treatment. No in vivo toxicity or other physiological complications were observed in all the animal groups for 21 days post hydrogel exposure as indicated by the maintenance of stable body weight and lack of necrosis at the site of administration. Therefore, our data indicate that the PL-loaded hydrogel is biocompatible. Based on these results we can conclude that the intracranial administration of PL via a dextran-dendrimer hydrogel offers a new alternative for GBM treatment.

TRPV2 is More Highly Expressed in Paired Recurrent GBMs

TRPV2 is associated with a more aggressive phenotype and we, therefore, decided to test primary and recurrent pairs of GBMs for TRPV2. Eleven primary and recurrent paired samples were analyzed on a nano-high-performance liquid chromatography electrospray ionisation mass spectrometer. TRPV2 was not differentially regulated between primary and recurrent samples. In fact, no peptide was detected in the mass spectrometry. When looking at archived data, we can see that TRPV2 is only detected in 88 out of 3299 deposited human studies, while GAPDH can be seen 336 times. Since TRPV2 has 6 transmembrane domains, which are highly hydrophobic, only studies using a hydrophobic specific lysis buffer can detect TRPV2. Therefore, we performed qRT-PCR to test the mRNA levels and, indeed, TRPV2 is more highly expressed in the recurrent population (FIG. 12). After signal normalization, proteins with missing values were removed and a paired T-test was performed. The ranked T value was analyzed using a pre-ranked GeneSet Enrichment Analysis (GSEA), whereas the significant proteins (p≤0.05 and fold change±1.5) were processed using Ingenuity Pathway Analysis (IPA). In the primary samples, we observed terms relating to gene and mRNA regulation, as well as, adhesion and protein localization. Oxidative phosphorylation and neurotransmitter signalling, both of which involve calcium transport, were upregulated in recurrent samples, suggesting that TRPV2 is more active in the recurrent samples. A heatmap for Hallmark Oxidative Phosphorylation, a top ranking geneset, is displayed showing that expression is indeed increased, however, at an individual sample level. Next, we looked at the IPA results and observed similar canonical pathways being regulated (FIG. 13). As can be seen in Table 2, mitochondrial dysfunction and oxidative phosphorylation are the top hits. We then performed an upstream analysis and selected 4 top candidates which involved mitochondrial dysfunction. We observed that RICTOR was active in the primary samples, which would lead to a repression of genes involved with oxidative phosphorylation. However, approximately a third of the proteins were not downregulated, suggesting that RICTOR may not be an upstream regulator of mitochondrial dysfunction. Instead, our results indicate that PPARGC1A (shown in FIG. 14 and the heatmap in FIG. 15), which is involved in mitochondrial biogenesis, is the potential upstream regulator responsible for the mitochondrial dysfunction and increase in oxidative phosphorylation in the recurrent tumors.

NPs and their biologically pre-validated architectures provide often-untapped opportunities to develop probes and drug leads for chemical biology and molecular medicine. Nonetheless, only a fraction of NPs have been tested for biological activity, in particular through phenotypic assays. Thus, there is an urgent need of identifying targets engaged at biologically relevant concentrations to enable informed drug design. A deep understanding of pharmacology networks, i.e. interconnection of on- and off-targets, offers a solution to design ligands to preferred polypharmacological profiles, and mitigate features that may lead to adverse drug reactions and attrition. Compound 1 has shown a promising anticancer profile despite structural liabilities. Using principles of pharmacophore similarity and a publicly available machine learning method we associate 1 to functional, ligand efficient and allosteric antagonism of TRPV2. Importantly, compound 1 displayed exquisite selectivity within the TRP channel family and may provide a prime source of inspiration for rational molecular design. Moreover, the result is unprecedented considering the prior inexistence of TRPV2 antagonists within NP chemical space. The mechanism characterized herein offers a previously hitherto unknown explanation for the observed anticancer and antimetastatic effects,[16] and potential target tractability. TRP channels are an emerging class of potential drug targets in the context of cancer,[48] but TRPV2 remains largely unexplored.[36] Although compound 1 entails features for selective TRPV2 modulation it should not be directly used as a TRPV2 chemical probe. In fact, engagement of STAT3 at identical concentrations[18] may lead to confounding assay readouts.

From a computational point of view our approach is dependent on the machine learning tool, superimposition algorithm and energy minimization force field. Hence, false positive predictions should also be expected. Nonetheless, our results show that 2D and 3D pharmacophore descriptors may be expeditiously employed to suggest and unveil new biology for bioactive chemical matter.

The data disclosed herein provide a platform for future exploration of TRPV2 in a cancer drug discovery context and potential value of 1 as a drug lead. Ultimately, we foresee broad scope and prime utility of related computational technologies for deconvoluting complex phenotypic readouts to a macromolecular level. This and related concepts may find applicability as a general approach in systems biology by leveraging the establishment of pharmacology networks in molecular medicine.

TABLE 1

| TRP channel | $IC_{50}$ / $\mu M$ ± SD |
|---|---|
| TRPV1 | >100 |
| TRPV2 | 4.6 ± 0.13 log units |
| TRPV3 | >100 |
| TRPV4 | >100 |
| TRPV5 | >100 |
| TRPA1 | 39 ± 0.15 log units |
| TRPC1 | >100 |
| TRPC3 | >100 |
| TRPC4 | >100 |
| TRPC5 | >100 |
| TRPC6 | >100 |
| TRPC7 | 64 ± 0.06 log units |
| TRPM2 | >100 |
| TRPM3 | >100 |
| TRPM4 | >100 |
| TRPM5 | >100 |
| TRPM8 | >100 |

Controls-TRPV2: tranilast ($IC_{50}$ = 2.3 $\mu M$ ± 0.25 log units); TRPA1: ruthenium red ($IC_{50}$ = 2.3 $\mu M$ ± 0.19 log units); TRPC7: SKF 96365 ($IC_{50}$ = 103 $\mu M$ ± 0.27 log units). All experiments were performed in duplicate.

TABLE 2

| Ingenuity Canonical Pathways | p value | Down Reg. | Up Reg. | No change |
|---|---|---|---|---|
| Mitochondrial Dysfunction | $6.3 \times 10^{-13}$ | 14/171 | 2/171 | 0/171 |
| Oxidative Phosphorylation | $7.9 \times 10^{-11}$ | 12/109 | 0/109 | 0/109 |
| Sirtuin Signaling Pathway | $2.3 \times 10^{-10}$ | 14/292 | 3/292 | 0/292 |
| Huntington's Disease Signaling | $3.5 \times 10^{-5}$ | 8/250 | 2/250 | 0/250 |
| Leucine Degradation I | $4.1 \times 10^{-15}$ | 1/9 | 2/9 | 0/9 |
| GP6 Signaling Pathway | 0.00010 | 3/134 | 4/134 | 0/134 |
| Glutamate Degradation II | 0.00019 | 2/3 | 0/3 | 0/3 |
| Aspartate Biosynthesis | 0.00019 | 2/3 | 0/3 | 0/3 |
| L-cysteine Degradation I | 0.00038 | 2/4 | 0/4 | 0/4 |
| mTOR Signaling | 0.00123 | 3/201 | 4/201 | 0/201 |

REFERENCES (1) Over, B.; Wetzel, S.; Grutter, C.; Nakai, Y.; Renner, S.; Rauh, D.; Waldmann, H. *Nat. Chem.* 2013, 5, 21-8.
(2) Rodrigues, T.; Reker, D.; Schneider, P.; Schneider, G. *Nat. Chem.* 2016, 8, 531-41.
(3) Clemons, P. A.; Bodycombe, N. E.; Carrinski, H. A.; Wilson, J. A.; Shamji, A. F.; Wagner, B. K.; Koehler, A. N.; Schreiber, S. L. *Proc. Natl. Acad. Sci. U.S.A.* 2010, 107, 18787-92.
(4) Harvey, A. L.; Edrada-Ebel, R.; Quinn, R. J. *Nat. Rev. Drug Discov.* 2015, 14, 111-29.
(5) van Hattum, H.; Waldmann, H. *J. Am. Chem. Soc.* 2014, 136, 11853-9.
(6) Kapoor, S.; Waldmann, H.; Ziegler, S. *Bioorg. Med. Chem.* 2016, 24, 3232-45.
(7) Reker, D.; Perna, A. M.; Rodrigues, T.; Schneider, P.; Reutlinger, M.; Monch, B.; Koeberle, A.; Lamers, C.; Gabler, M.; Steinmetz, H.; Muller, R.; Schubert-Zsilavecz, M.; Werz, O.; Schneider, G. *Nat. Chem.* 2014, 6, 1072-8.

(8) Schneider, G.; Reker, D.; Chen, T.; Hauenstein, K.; Schneider, P.; Altmann, K. H. *Angew. Chem. Int. Ed.* 2016, 55, 12408-11.
(9) Rodrigues, T.; Reker, D.; Kunze, J.; Schneider, P.; Schneider, G. *Angew. Chem. Int. Ed.* 2015, 54, 10516-20.
(10) Reker, D.; Rodrigues, T.; Schneider, P.; Schneider, G. *Proc. Natl. Acad. Sci. U.S.A.* 2014, 111, 4067-72.
(11) Ratnayake, R.; Covell, D.; Ransom, T. T.; Gustafson, K. R.; Beutler, J. A. *Org. Lett.* 2009, 11, 57-60.
(12) Akbulut, Y.; Gaunt, H. J.; Muraki, K.; Ludlow, M. J.; Amer, M. S.; Bruns, A.; Vasudev, N. S.; Radtke, L.; Willot, M.; Hahn, S.; Seitz, T.; Ziegler, S.; Christmann, M.; Beech, D. J.; Waldmann, H. *Angew. Chem. Int. Ed.* 2015, 54, 3787-91.
(13) Carson, C.; Raman, P.; Tullai, J.; Xu, L.; Henault, M.; Thomas, E.; Yeola, S.; Lao, J.; McPate, M.; Verkuyl, J. M.; Marsh, G.; Sarber, J.; Amaral, A.; Bailey, S.; Lubicka, D.; Pham, H.; Miranda, N.; Ding, J.; Tang, H. M.; Ju, H.; Tranter, P.; Ji, N.; Krastel, P.; Jain, R. K.; Schumacher, A. M.; Loureiro, J. J.; George, E.; Berellini, G.; Ross, N. T.; Bushell, S. M.; Erdemli, G.; Solomon, J. M. *PLoS One* 2015, 10, e0127498.
(14) Friedrich, L.; Rodrigues, T.; Neuhaus, C. S.; Schneider, P.; Schneider, G. *Angew. Chem. Int. Ed.* 2016, 55, 6789-92
(15) Rodrigues, T.; Sieglitz, F.; Somovilla, V. J.; Cal, P. M.; Galione, A.; Corzana, F.; Bernardes, G. J. L. *Angew. Chem. Int. Ed.* 2016, 55, 11077-81.
(16) Raj, L.; Ide, T.; Gurkar, A. U.; Foley, M.; Schenone, M.; Li, X.; Tolliday, N. J.; Golub, T. R.; Carr, S. A.; Shamji, A. F.; Stern, A. M.; Mandinova, A.; Schreiber, S. L.; Lee, S. W. *Nature* 2011, 475, 231-4.
(17) Adams, D. J.; Dai, M.; Pellegrino, G.; Wagner, B. K.; Stern, A. M.; Shamji, A. F.; Schreiber, S. L. *Proc. Natl. Acad. Sci. U.S.A.* 2012, 109, 15115-20.
(18) Bharadwaj, U.; Eckols, T. K.; Kolosov, M.; Kasembeli, M. M.; Adam, A.; Torres, D.; Zhang, X.; Dobrolecki, L. E.; Wei, W.; Lewis, M. T.; Dave, B.; Chang, J. C.; Landis, M. D.; Creighton, C. J.; Mancini, M. A.; Tweardy, D. J. *Oncogene* 2015, 34, 1341-53.
(19) Pertwee, R. G. *Br. J. Pharmacol.* 2008, 153, 199-215.
(20) Baell, J. B.; Holloway, G. A. *J. Med. Chem.* 2010, 53, 2719-40.
(21) Walters, W. P.; Ajay; Murcko, M. A. *Curr. Opin. Chem. Biol.* 1999, 3, 384-7.
(22) Witte, D. G.; Cassar, S. C.; Masters, J. N.; Esbenshade, T.; Hancock, A. A. *J. Biomol. Screen.* 2002, 7, 466-75.
(23) Yang, S.; Yang, F.; Wei, N.; Hong, J.; Li, B.; Luo, L.; Rong, M.; Yarov-Yarovoy, V.; Zheng, J.; Wang, K.; Lai, R. *Nat. Commun.* 2015, 6, 8297.
(24) Shoemaker, R. H. *Nat. Rev. Cancer* 2006, 6, 813-23.
(25) Yuan, H.; Houck, K. L.; Tian, Y.; Bharadwaj, U.; Hull, K.; Zhou, Z.; Zhu, M.; Wu, X.; Tweardy, D. J.; Romo, D.; Fu, X.; Zhang, Y.; Zhang, J.; Dong, J. F. *PLoS One* 2015, 10, e0143964.
(26) Zheng, J.; Son, D. J.; Gu, S. M.; Woo, J. R.; Ham, Y. W.; Lee, H. P.; Kim, W. J.; Jung, J. K.; Hong, J. T. *Sci. Rep.* 2016, 6, 26357.
(27) Mootha, V. K.; Lindgren, C. M.; Eriksson, K. F.; Subramanian, A.; Sihag, S.; Lehar, J.; Puigserver, P.; Carlsson, E.; Ridderstrale, M.; Laurila, E.; Houstis, N.; Daly, M. J.; Patterson, N.; Mesirov, J. P.; Golub, T. R.; Tamayo, P.; Spiegelman, B.; Lander, E. S.; Hirschhorn, J. N.; Altshuler, D.; Groop, L. C. *Nat. Genet.* 2003, 34, 267-73.
(28) Subramanian, A.; Tamayo, P.; Mootha, V. K.; Mukherjee, S.; Ebert, B. L.; Gillette, M. A.; Paulovich, A.; Pomeroy, S. L.; Golub, T. R.; Lander, E. S.; Mesirov, J. P. *Proc. Natl. Acad. Sci. U.S.A.* 2005, 102, 15545-50.
(29) Hayden, M. S.; West, A. P.; Ghosh, S. *Oncogene* 2006, 95, 6758-80.
(30) The GTEx Consortium. *Nat. Genet.* 2013, 45, 580-5.
(31) The GTEx Consortium. *Science* 2015, 348, 648-60.
(32) Tomida, S.; Takeuchi, T.; Shimada, Y.; Arima, C.; Matsuo, K.; Mitsudomi, T.; Yatabe, Y.; Takahashi, T. *J. Clin. Oncol.* 2009, 27, 2793-9.
(33) Baty, F.; Facompre, M.; Kaiser, S.; Schumacher, M.; Pless, M.; Bubendorf, L.; Savic, S.; Marrer, E.; Budach, W.; Buess, M.; Kehren, J.; Tamm, M.; Brutsche, M. H. *Am. J. Respir. Crit. Care Med.* 2010, 181, 181-8.
(34) Rousseaux, S.; Debernardi, A.; Jacquiau, B.; Vitte, A. L.; Vesin, A.; Nagy-Mignotte, H.; Moro-Sibilot, D.; Brichon, P. Y.; Lantuejoul, S.; Hainaut, P.; Laffaire, J.; de Reynies, A.; Beer, D. G.; Timsit, J. F.; Brambilla, C.; Brambilla, E.; Khochbin, S. *Sci. Transl. Med.* 2013, 5, 186ra66.
(35) Girard, L.; Rodriguez-Canales, J.; Behrens, C.; Thompson, D. M.; Botros, I. W.; Tang, H.; Xie, Y.; Rekhtman, N.; Travis, W. D.; Wistuba, II; Minna, J. D.; Gazdar, A. F. *Clin. Cancer Res.* 2016, 22, 4880-9.
(36) Peralvarez-Marin, A.; Donate-Macian, P.; Gaudet, R. *FEBS J.* 2013, 280, 5471-87.
(37) Gambade, A.; Zreika, S.; Gueguinou, M.; Chourpa, I.; Fromont, G.; Bouchet, A. M.; Burlaud-Gaillard, J.; Potier-Cartereau, M.; Roger, S.; Aucagne, V.; Chevalier, S.; Vandier, C.; Goupille, C.; Weber, G. *Oncotarget* 2016, 7, 23785-800.
(38) Monet, M.; Gkika, D.; Lehen'kyi, V.; Pourtier, A.; Vanden Abeele, F.; Bidaux, G.; Juvin, V.; Rassendren, F.; Humez, S.; Prevarsakaya, N. *Biochim. Biophys. Acta* 2009, 1793, 528-39.
(39) Liberati, S.; Morelli, M. B.; Amantini, C.; Farfariello, V.; Santoni, M.; Conti, A.; Nabissi, M.; Cascinu, S.; Santoni, G. *Cells* 2014, 3, 112-28.
(40) Ma, W.; Li, C.; Yin, S.; Liu, J.; Gao, C.; Lin, Z.; Huang, R.; Huang, J.; Li, Z. *Free Radic. Biol. Med.* 2015, 89, 1003-13.
(41) Transfection of HepG2 cells with the TRPV2-RFP fusion protein, and TRPV2 gene silencing with siRNA were not successful. Taking into account reports correlating TRPV2 expression with migration, our data supports target tractability and provides a rationale for hit-to-lead and lead optimization campaigns.
(42) Dorsam, R. T.; Gutkind, J. S. *Nat. Rev. Cancer* 2007, 7, 79-94.
(43) O'Hayre, M.; Salanga, C. L.; Handel, T. M.; Allen, S. J. *Biochem. J.* 2008, 409, 635-49.
(44) Wu, J.; Xie, N.; Zhao, X.; Nice, E. C.; Huang, C. *Cancer Genomics Proteomics* 2012, 9, 37-50.
(45) Huang, C.; Jacobson, K.; Schaller, M. D. *J. Cell. Sci.* 2004, 117, 4619-28.
(46) Schwab, A.; Fabian, A.; Hanley, P. J.; Stock, C. *Physiol. Rev.* 2012, 92, 1865-913.
(47) ENCODE Project Consortium. *Nature* 2012, 489, 57-74.
(48) Rodrigues, T.; Sieglitz, F.; Bernardes, G. J. *Chem. Soc. Rev.* 2016, 45, 6130-7.

The invention claimed is:

1. A method of treating cancer characterized by transient receptor potential vanilloid 2 channel (TRPV2) expression comprising: providing a sample of cancer cells from a cancer patient, determining TRPV2 expression in the cancer cells, and administering a piperlongumine compound to the patient if TRPV2 is expressed in the cancer cells.

2. The method according to claim 1 wherein the piperlongumine compound is a reversible antagonist of TRPV2.

3. The method according to claim 1 wherein the piperlongumine compound is piperlongumine or an analogue, derivative or prodrug thereof.

4. The method according to claim 3 wherein the piperlongumine compound has the formula 1:

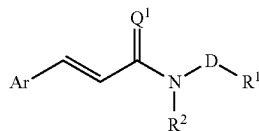

where $Q^1$ is O or S,
—Ar is an optionally substituted aryl group,
-D- is selected from —C(O)—, —C(S)—, —CH(OH)— and —CH(SH)—, and
—$R^1$ and —$R^2$, together with —N-D- to which they are attached, form an optionally substituted heterocyclic ring, or —$R^1$ and —$R^2$ are each independently selected from hydrogen and optionally substituted alkyl, alkenyl, alkynyl, cycloalkyl, heterocyclyl and aryl, and salts, solvates and protected forms thereof.

5. The method according to claim 4, wherein $Q^1$ is O.

6. The method according to claim 3, wherein -D- is —C(O)— or —C(S)—.

7. The method according to any one of claim 4, wherein —$R^1$ and —$R^2$, together with —N-D- to which they are attached, form an optionally substituted heterocyclic ring.

8. The method according to claim 7, wherein the heterocyclic ring is partially unsaturated.

9. The method according to claim 8, wherein -D- is —C(O)— or —C(S)—, and the unsaturation is conjugated with the —C(O)— or —C(S)—.

10. The method according to claim 9, wherein the heterocyclic ring is a 4- to 9-membered ring.

11. The method according to any one of claim 10, wherein —$R^1$ and —$R^2$, together with —N-D- to which they are attached, form a β-unsaturated δ-lactam.

12. The method according to claim 4, wherein Ar— is an optionally substituted carboaryl group, or an optionally substituted heteroaryl group.

13. The method according to claim 12, wherein Ar— is optionally substituted phenyl.

14. The method according to any one of claim 13, wherein Ar— is phenyl substituted with one or more groups selected from halo, cyano, —$R^{S1}$, —OH, —$OR^{S1}$, —SH, —$SR^{S1}$, —$NH_2$, —$NHR^{S1}$, —$NR^{S1}R^{S2}$, —COON, —$CONH_2$, —$CONHR^{S1}$, —$CONR^{S1}R^{S2}$, $NHCOR^{S1}$, —$N(R^{S1})COR^{S1}$, where each —$R^{S1}$ and each —$R^{S2}$ is independently alkyl, alkenyl, alkynyl, aryl or aralkyl, which are optionally substituted with halo, or —$R^{S1}$ and —$R^{S2}$ may together form a heterocyclic ring.

15. The method according to claim 1 wherein cancer is a skin cancer, breast cancer, prostate cancer, brain cancer or blood cancer.

16. The method according to claim 15 wherein the cancer is a metastatic cancer.

17. The method according to claim 1 wherein the piperlongumine compound is encapsulated in a hydrogel.

18. The method of claim 6, wherein -D- is —C(O).

19. The method of claim 10, wherein the heterocyclic ring is a 4- to 6-membered ring.

20. The method of claim 19, wherein the heterocyclic ring is a 6-membered ring.

21. The method of claim 11, wherein —R1 and —R2, together with —N-D- to which they are attached is 5,6-dihydropyridin-2-one-1-yl.

22. The method of claim 12, wherein Ar— is phenyl, pyridinyl, pyrimidinyl, furanyl, thiophenyl, or pyrrolyl.

23. The method of claim 1, wherein the piperlongumine compound is piperlongumine.

24. The method of claim 1, wherein TRPV2 expression is determined by a technique selected from PCR-based method, ELISA, immunofluorescent assay, chemiluminescent assay, and immunohistochemistry.

25. The method of claim 23, wherein the technique comprises reverse transcription PCR.

26. The method of claim 1, wherein the patient is a mammal.

27. The method of claim 25, wherein the patient is a human.

28. The method of claim 1, wherein the piperlongumine compound is administered to the patient if TRPV2 is expressed in one or more cancer cells greater than a predetermined threshold value.

* * * * *